United States Patent
Vonnegut et al.

(10) Patent No.: US 10,556,920 B2
(45) Date of Patent: Feb. 11, 2020

(54) PHOSPHORUS-CONTAINING HETEROCYCLES AND A METHOD FOR MAKING AND USING

(71) Applicant: University of Oregon, Eugene, OR (US)

(72) Inventors: Chris Vonnegut, Springfield, OR (US); Airlia Shonkwiler, West Linn, OR (US); Michael Haley, Eugene, OR (US); Darren Johnson, Eugene, OR (US)

(73) Assignee: University of Oregon, Eugene, OR (US)

( * ) Notice: Subject to any disclaimer, the term of this patent is extended or adjusted under 35 U.S.C. 154(b) by 0 days.

(21) Appl. No.: 15/850,388

(22) Filed: Dec. 21, 2017

(65) Prior Publication Data

US 2018/0118769 A1    May 3, 2018

Related U.S. Application Data

(63) Continuation-in-part of application No. PCT/US2016/038813, filed on Jun. 22, 2016.

(60) Provisional application No. 62/183,477, filed on Jun. 23, 2015.

(51) Int. Cl.
| | |
|---|---|
| *C07F 9/6584* | (2006.01) |
| *A61K 31/395* | (2006.01) |
| *A61K 31/662* | (2006.01) |
| *C07F 9/6571* | (2006.01) |
| *C09K 11/06* | (2006.01) |

(52) U.S. Cl.
CPC ........ *C07F 9/65846* (2013.01); *A61K 31/395* (2013.01); *A61K 31/662* (2013.01); *C07F 9/657172* (2013.01); *C09K 11/06* (2013.01); *C09K 2211/104* (2013.01)

(58) Field of Classification Search
CPC ........... C07F 9/657172; C07F 9/65846; C09K 2211/104
See application file for complete search history.

(56) References Cited

U.S. PATENT DOCUMENTS

| | | | |
|---|---|---|---|
| 4,559,117 A | 12/1985 | Bohm | |
| 4,727,144 A | 2/1988 | Chen et al. | |
| 5,378,713 A | 1/1995 | Press et al. | |
| 5,750,409 A | 5/1998 | Hermann et al. | |
| 6,818,313 B2 | 11/2004 | Phelps et al. | |
| 7,235,142 B2 | 6/2007 | Sturgill et al. | |
| 7,291,217 B2 | 11/2007 | Phelps et al. | |
| 7,294,211 B2 | 11/2007 | Sturgill et al. | |
| 7,407,711 B2 | 8/2008 | Phelps et al. | |
| 7,422,793 B2 | 9/2008 | Phelps et al. | |
| 7,537,663 B2 | 5/2009 | Phelps et al. | |
| 7,789,958 B2 | 11/2010 | Sturgill et al. | |
| 7,833,331 B2 | 11/2010 | Sturgill et al. | |
| 8,012,603 B2 | 9/2011 | Doi et al. | |
| 8,142,908 B2 | 3/2012 | Nakatani et al. | |
| 8,765,803 B1 | 7/2014 | Wandinger-Ness et al. | |
| 2003/0230363 A1 | 12/2003 | Sturgill et al. | |
| 2003/0234063 A1 | 12/2003 | Sturgill et al. | |
| 2004/0011252 A1 | 1/2004 | Sturgill et al. | |
| 2004/0016363 A1 | 1/2004 | Phelps et al. | |
| 2004/0016910 A1 | 1/2004 | Phelps et al. | |
| 2004/0020568 A1 | 2/2004 | Phelps et al. | |
| 2004/0104377 A1 | 6/2004 | Phelps et al. | |
| 2004/0231754 A1 | 11/2004 | Phelps et al. | |
| 2007/0020479 A1 | 1/2007 | Uetani et al. | |
| 2007/0051922 A1 | 3/2007 | Nakatani et al. | |

(Continued)

FOREIGN PATENT DOCUMENTS

| | | |
|---|---|---|
| EP | 0124607 | 11/1984 |
| EP | 1472319 | 11/2004 |

(Continued)

OTHER PUBLICATIONS

Kamel (European Journal of Medicinal Chemistry 51 (2012) 239-249).*
Liu (Org. Lett. 2015, 17, 2046-2049).*
Ali et al., "Synthetic Methods for Phosphorus Compounds Containing Pyrazole Rings," *Heterocycles* 85(9):2073-2109, Jun. 25, 2012.

(Continued)

*Primary Examiner* — Valerie Rodriguez-Garcia
(74) *Attorney, Agent, or Firm* — Klarquist, Sparkman, LLP

(57) ABSTRACT

Disclosed embodiments concern a phosphorus-containing heterocyclic compound according to the formula

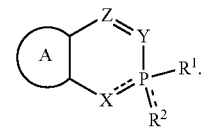

One exemplary compound is

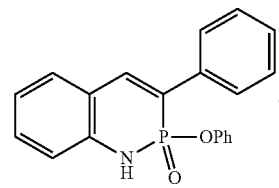

Certain embodiments fluoresce with excitation by light. The compounds are useful as fluorescent probes and as bioisosteres. In some embodiments, the compounds are bioisosteres of alpha-quinolones. Also disclosed is a method for making the compounds.

17 Claims, 8 Drawing Sheets

(56) References Cited

U.S. PATENT DOCUMENTS

| | | |
|---|---|---|
| 2007/0149673 A1 | 6/2007 | Sturgill et al. |
| 2008/0138651 A1 | 6/2008 | Doi et al. |
| 2009/0039765 A1 | 2/2009 | Uetani et al. |
| 2009/0163628 A1 | 6/2009 | Sturgill et al. |
| 2009/0212693 A1 | 8/2009 | Yamada |
| 2010/0165604 A1 | 7/2010 | Uetani |
| 2010/0330380 A1 | 12/2010 | Colreavy et al. |
| 2012/0008068 A1 | 1/2012 | Doi et al. |

FOREIGN PATENT DOCUMENTS

| | | |
|---|---|---|
| EP | 1767529 | 5/2009 |
| EP | 2063473 | 5/2009 |
| EP | 2220176 | 8/2010 |
| EP | 2325223 | 5/2011 |
| EP | 2325226 | 5/2011 |
| EP | 2603500 | 11/2014 |
| JP | 56043250 * | 4/1981 |
| WO | WO 1984/001951 | 5/1984 |
| WO | WO 2003/060019 | 7/2003 |
| WO | WO 2003/060191 | 7/2003 |
| WO | WO 2003/060192 | 7/2003 |
| WO | WO 2004/009869 | 1/2004 |
| WO | WO 2004/065305 | 8/2004 |
| WO | WO 2009/069111 | 6/2009 |
| WO | WO 2009/105348 | 8/2009 |
| WO | WO 2010/105851 | 9/2010 |
| WO | WO 2014/183217 | 11/2014 |

OTHER PUBLICATIONS

Barluenga et al., "A Simple Synthesis of the First 1-$2^{\lambda\text{-}5}$ 5-Benzazaphosphinine Ring," *Tetrahedron Letters* 28(37)4327-4328, 1987.

Dewar et al., "New Heteroaromatic Compounds. Part IV. Novel Heterocyclic Compounds of Phosphorus," *Journal of the American Chemical Society* 82(21):5685-5688, 1960.

Marshall et al., "The Haemodynamic and Metabolic Effects of MG 8926, A Prospective Antidysrhythmic and Antianginal Agent," *British Journal of Pharmacology* 59(2):311-322, Feb. 1977.

Pubchem. CID 11850407, https://pubchem.ncib.nim.nih.gov/compound/11850407#section=Top>. pp. 1-9, Nov. 6, 2006.

Pubchem. Schembl 14363751, https://pubchem.ncib.nim.nih.gov/compund/58996082#section=Top>, pp. 1-11, Aug. 19, 2012.

Pubchem. Schembl 3071169, https://pubchem.ncib.nim.nih.gov/compound/68501025#section=Top>, pp. 1-10, Nov. 30, 2012.

Pubchem. Schembl 487879, https://pubchem.ncib.nim.nih.gov/compound/667017#section=Top>, pp. 1-10, Nov. 30, 2012.

Pubchem. Schembl 90724458, https://pubchem.ncib.nim.nih.gov.compound/90724458>, pp. 1-10, Mar. 16, 2015.

Tang et al., "Synthesis of Phosphaisoquinolin-l-ones by Pd(II)-Catalyzed Cyclization of o-(1-Alkynyl)phenylphosphonamide Monoesters," *The Journal of Organic Chemistry* 71(22):8489-8492, 2006.

Tang et al., "Pd(II)-catalyzed coupling-cyclization reaction of o-ethylnylphenylphosphonamides monoesters with allyl halide," *Tetrahedron* 64(46):10507-10511, Nov. 10, 2008.

Yan et al., "High-throughput screening of novel antagonists on melanin-concentrating hormone receptor-1," *Acta Pharmacologica Sinica* 29(6):752-758, Jun. 2008.

* cited by examiner

PHOSPHORUS-CONTAINING HETEROCYCLES AND A METHOD FOR MAKING AND USING

CROSS REFERENCE TO RELATED APPLICATION

This application is a continuation-in-part of International Application No. PCT/US2016/038813, filed on Jun. 22, 2016, which was published in English under PCT Article 21(2), which in turn claims the benefit of the earlier filing date of U.S. provisional patent application No. 62/183,477, filed Jun. 23, 2015, each of which is incorporated herein by reference in its entirety.

ACKNOWLEDGMENT OF GOVERNMENT SUPPORT

This invention was made with government support under grant No. R01-GM087398 awarded by the National Institutes of Health. The government has certain rights in the invention.

SUMMARY

Disclosed herein are embodiments of a compound having a formula

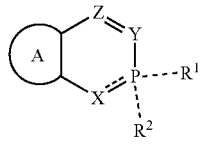

or a pharmaceutically acceptable salt thereof, wherein ring A is aryl, heteroaryl, cycloaliphatic or heterocyclic; X is O, S, SO, $SO_2$, or $NR^3$; Y is N or $CR^4$; Z is $CR^4$, such as CH, or N; $R^1$ is —OH, aliphatic, aryl, heteroaryl, heterocyclic, heteroaliphatic, —O-aliphatic, —O-aryl, —O— heteroaryl, —O-heterocyclic, or —O-heteroaliphatic; $R^2$ is oxo (═O), ═S, ═Se, —OH, aliphatic, aryl, heteroaryl, heterocyclic, heteroaliphatic, —O-aliphatic, —O-aryl, —O-heteroaryl, —O-heterocyclic, or —O-heteroaliphatic; $R^3$ is H, aliphatic, heteroaliphatic, aryl, heterocyclic, heteroaryl, acyl, carboxyl ester, or a lone pair of electrons; and each $R^4$ independently is H, aliphatic, heteroaliphatic, aryl, heterocyclic, heteroaryl, halo, CN, $NO_2$, sulfonyl, amino, carboxyl, carboxyl ester, aminosulfonyl, or aminocarbonyl.

In some embodiments, $R^1$ is —OH, alkyl, alkenyl, alkynyl, cycloalkyl, cycloalkenyl, cycloalkynyl, aryl, heteroaryl, heterocyclic, heterocycloaliphatic, heteroalkyl, heterocycloalkyl, —O-alkyl, —O-alkenyl, —O-alkynyl, —O-cycloalkyl, —O-cycloalkenyl, —O-cycloalkynyl, —O-aryl, —O— heteroaryl, —O-heterocyclic, —O-heterocycloaliphatic, —O-heteroalkyl or —O-heterocycloalkyl. $R^1$ may be —O-phenyl, methoxy, ethoxy, propoxy, cyclopropoxy, isopropoxy, butoxy, isobutoxy, tert-butoxy, phenyl, pyridyl, thienyl, methyl, ethyl, propyl, cyclopropyl, isopropyl, n-butyl, isobutyl, sec-butyl, or tert-butyl, and in certain embodiments, $R^1$ is —O-phenyl, phenyl, or thienyl.

$R^2$ may be oxo, —OH, alkyl, alkenyl, alkynyl, cycloalkyl, cycloalkenyl, cycloalkynyl, aryl, heteroaryl, heterocyclic, heterocycloaliphatic, heteroalkyl, heterocycloalkyl, —O-alkyl, —O— alkenyl, —O-alkynyl, —O-cycloalkyl, —O-cycloalkenyl, —O-cycloalkynyl, —O-aryl, —O-heteroaryl, —O-heterocyclic, —O-heterocycloaliphatic, —O-heteroalkyl or —O-heterocycloalkyl. In certain examples, $R^2$ is —OH, aliphatic, aryl, heteroaryl, heterocyclic, heteroaliphatic, —O-aliphatic, —O-aryl, —O-heteroaryl, —O-heterocyclic, or —O-heteroaliphatic.

$R^3$ may be H, alkyl, alkenyl, alkynyl, cycloalkyl, cycloalkenyl, cycloalkynyl, aryl, heteroaryl, heterocyclic, heterocycloaliphatic, heteroalkyl, heterocycloalkyl, carboxyl ester, or a lone pair of electrons. And/or each $R^4$ independently may be H, alkyl, alkenyl, alkynyl, haloalkyl, cycloalkyl, cycloalkenyl, cycloalkynyl, aryl, heteroaryl, heterocyclic, heterocycloaliphatic, heteroalkyl, heterocycloalkyl, halo, CN, $NO_2$, sulfonyl, amino, carboxyl, carboxyl ester, aminosulfonyl, or aminocarbonyl. In some embodiments, each $R^4$ independently is alkyl, cycloalkyl, aryl or heteroaryl, and may be 2-pyridyl, phenyl, 4-NC-phenyl, 4-EtOC(O)-phenyl, 4-methoxyphenyl, 3,5-bis(trifluoromethyl)phenyl, methyl, ethyl, n-propyl, isopropyl, cyclopropyl, n-butyl, isobutyl, sec-butyl, tert-butyl, cyclobutyl, n-pentyl or cyclopentyl.

Ring A may be phenyl, naphthyl, benzodioxinyl, benzodioxolyl, quinolinyl, pyridinyl, pyrimidinyl, pyrazinyl, thienyl, furanyl, imidazolyl, pyrazolyl, oxazolyl, thiazolyl, triazolyl, oxadiazolyl or thiadiazolyl.

In certain embodiments, Z is CH and Y is $CR^4$.

In some embodiments, the compound has a formula

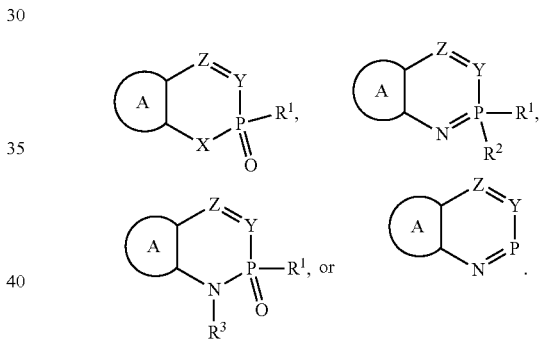

With respect to these formulas, X may be O, S, SO or $SO_2$; and/or $R^2$, if present, may be —OH, aliphatic, aryl, heteroaryl, heterocyclic, heteroaliphatic, —O-aliphatic, —O-aryl, —O-heteroaryl, —O-heterocyclic, or —O-heteroaliphatic.

With respect to any one of the above formulas, ring A may be phenyl, naphthyl, benzodioxinyl, benzodioxolyl, quinolinyl, pyridinyl, pyrimidinyl, pyrazinyl, thienyl, furanyl, imidazolyl, pyrazolyl, oxazolyl, thiazolyl, triazolyl, oxadiazolyl or thiadiazolyl, and in certain embodiments, ring A is phenyl, thienyl or naphthyl, and preferably is phenyl.

In certain embodiments, the compound has a formula

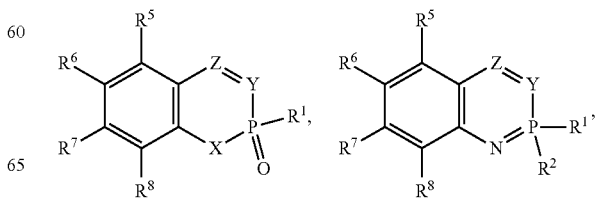

-continued

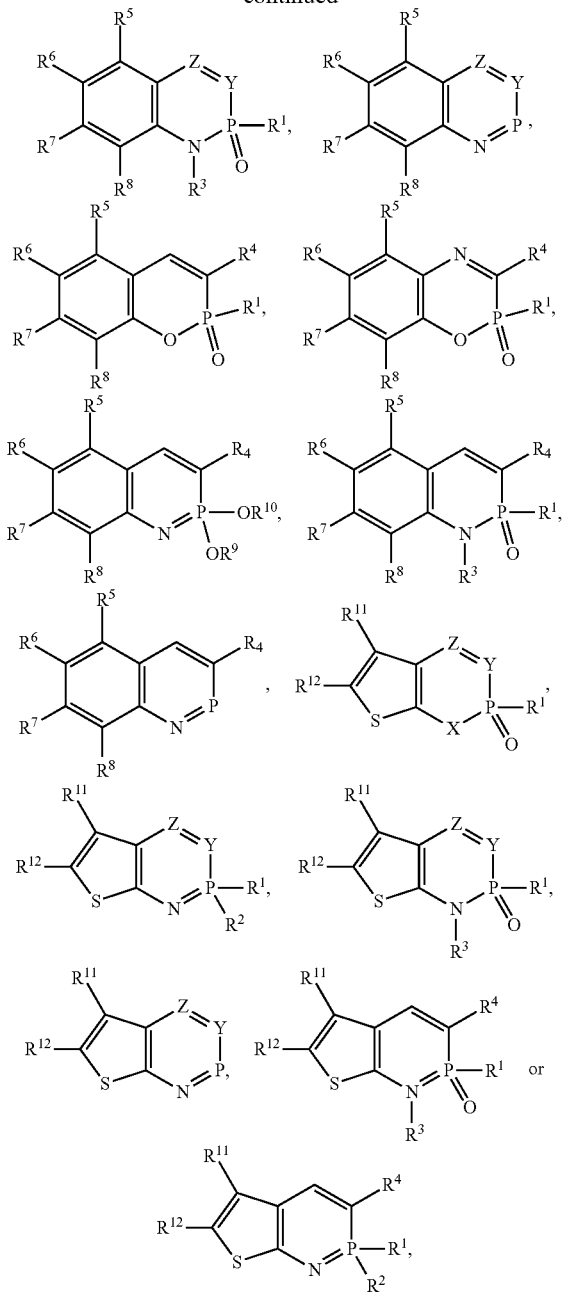

where $R^5$, $R^6$, $R^7$ $R^8$, $R^{11}$, and $R^{12}$ independently may be H, aliphatic, haloalkyl, heteroaliphatic, aryl, heterocyclic, heteroaryl, —O-aliphatic, —O-heteroaliphatic, —O-heterocyclic, —O-heteroaryl, —O-aryl, halo, OH, CN, $NO_2$, sulfonyl, amino, carboxyl, carboxyl ester, aminosulfonyl, or aminocarbonyl or any two adjacent groups together form an aliphatic, heterocyclic, aryl or heteroaryl ring. In some embodiments, $R^5$, $R^6$, $R^7$ $R^8$, $R^{11}$, and $R^{12}$ independently are H, alkyl, alkenyl, alkynyl, cycloalkyl, cycloalkenyl, cycloalkynyl, haloalkyl, aryl, heteroaryl, heterocyclic, heterocycloaliphatic, heteroalkyl, heterocycloalkyl, —O-alkyl, —O-alkenyl, —O— alkynyl, —O-heteroaliphatic, —O-heterocyclic, —O-heteroaryl, —O-aryl, halo, CN, $NO_2$, sulfonyl, amino, carboxyl, carboxyl ester, aminosulfonyl, or aminocarbonyl or any two adjacent groups together form an aliphatic, heterocyclic, aryl or heteroaryl ring. $R^9$ and $R^{10}$ independently may be aryl, aliphatic, heterocyclic or heteroaryl. In certain embodiments, $R^9$ and $R^{10}$ are phenyl, pyridyl, methyl, ethyl, propyl, cyclopropyl, isopropyl, butyl, isobutyl or tert-butyl, and preferably are phenyl. In other embodiments, $R^1$, if present, is —O-phenyl, $R^2$, if present, is —O— phenyl, or both. In some embodiments, Z is CH or N, typically CH, and/or Y is $CR^4$.

Each $R^4$ independently may be alkyl, cycloalkyl, aryl or heteroaryl, and may be selected from 2-pyridyl, phenyl, 4-NC-phenyl, 4-EtOC(O)-phenyl, 4-methoxyphenyl, 3,5-bis (trifluoromethyl)phenyl, methyl, ethyl, n-propyl, isopropyl, cyclopropyl, n-butyl, isobutyl, sec-butyl, tert-butyl, cyclobutyl, n-pentyl or cyclopentyl.

In other embodiments, the compound has a formula

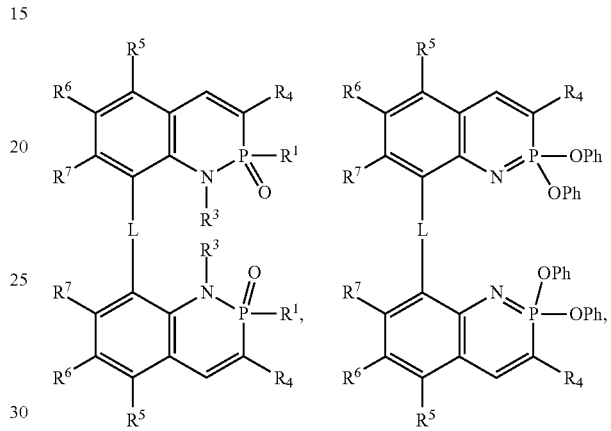

wherein $R^1$, $R^3$, $R^4$, $R^5$, $R^6$, and $R^7$ are as previously defined and L is phenyl, such as 1,2-substituted phenyl, 1,3-substituted phenyl, or 1,4-substituted phenyl.

Also disclosed herein are embodiments of a fluorescent probe comprising a compound disclosed herein. The fluorescent probe may comprise a targeting moiety, and in some embodiments, the targeting moiety is an antibody, hapten, nucleic acid sequence, or polypeptide.

A method for making the compounds is also disclosed herein. The method may comprise combining a triphenylphosphite with a compound having a formula

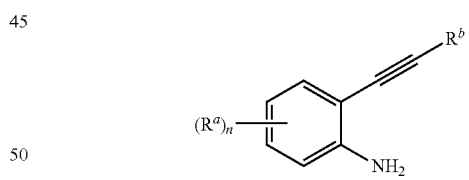

to form a mixture. With reference to this formula, each $R^a$ independently is aliphatic, haloalkyl, heteroaliphatic, aryl, heterocyclic, heteroaryl, halo, CN, $NO_2$, sulfonyl, amino, carboxyl, carboxyl ester, aminosulfonyl, or aminocarbonyl or any two adjacent $R^a$s together form an aliphatic, heterocyclic, aryl or heteroaryl ring; $R^b$ is H, alkyl, alkenyl, alkynyl, haloalkyl such as $CF_3$, cycloalkyl, cycloalkenyl, cycloalkynyl, aryl, heteroaryl, heterocyclic, heterocycloaliphatic, heteroalkyl, heterocycloalkyl, halo, CN, $NO_2$, sulfonyl, amino, carboxyl, carboxyl ester, aminosulfonyl, or aminocarbonyl; and n is 0, 1, 2, 3 or 4.

The mixture is then heated. Heating the mixture may comprise heating the mixture under an inert atmosphere. Additionally, the method may further comprises isolating a compound having a formula

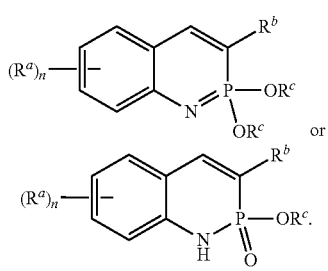

The foregoing and other objects, features, and advantages of the invention will become more apparent from the following detailed description, which proceeds with reference to the accompanying figures.

DETAILED DESCRIPTION

I. Terms

Figure 1:
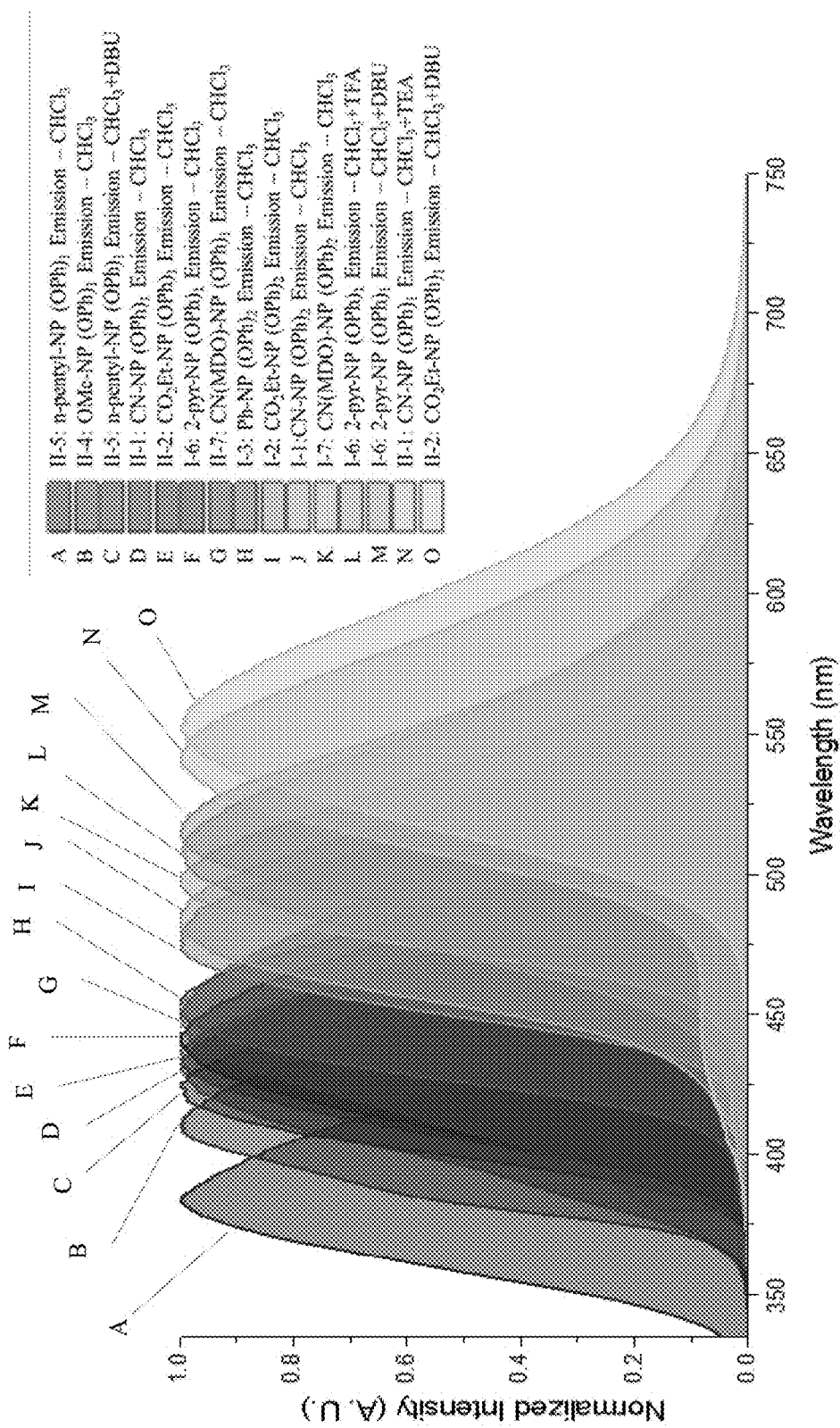
FIG. 1 is plot of intensity versus wavelength, illustrating the fluorescence emissions of various disclosed compounds.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference.

All numbers expressing quantities of components, molecular weights, percentages, temperatures, times, and so forth, as used in the specification or claims are to be understood as being modified by the term "about" unless expressly stated otherwise or the context is properly understood by a person of ordinary skill in the art to have a more definitive construction.

Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is recited.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

A wavy line "〰" or "〜" or an arrow "→" denoted a point of attachment of a group or moiety to the parent structure.

A dashed line "---" represents a bond that may or may not be present, and a "---R" group represents an optional group, i.e. a group that may or may not be present. A person of ordinary skill in the art will appreciate that in embodiments where a particular bond and/or group is not present, sufficient implicit hydrogens, lone pairs of electrons and/or other optional groups and/or bonds are present to ensure that the molecule maintains a correct valency at each atom.

When chemical structures are depicted or described, unless explicitly stated otherwise, all carbons are assumed to include hydrogen so that each carbon conforms to a valence of four.

For example, in the structure on the left-hand side of the schematic below there are nine hydrogen atoms implied. The nine hydrogen atoms are depicted in the right-hand structure.

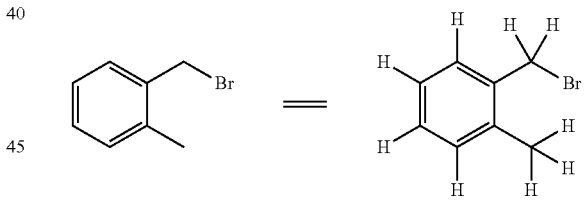

Sometimes a particular atom in a structure is described in textual formula as having a hydrogen or hydrogen atoms, for example —$CH_2CH_2$—. It will be understood by a person of ordinary skill in the art that the aforementioned descriptive techniques are common in the chemical arts to provide brevity and simplicity to description of organic structures.

A person of ordinary skill in the art will appreciate that the definitions may be combined to further describe a particular compound. For example, hydroxyaliphatic refers to an aliphatic group substituted with an hydroxy (—OH) group, and haloalkylaryl refers to an aryl group substituted with an alkyl group, where the alkyl group too is substituted with a halogen, and where the point of attachment to the parent structure is via the aryl moiety since aryl is the base name of the substituent.

All groups stated herein are understood to include both substituted and unsubstituted forms unless specifically stated otherwise, or context indicates otherwise. "Substituted" means that one or more hydrogen atoms of the specified group or moiety is each, independently of one another, replaced with the same or a different non-hydrogen substituent.

In some embodiments, exemplary substituent groups can include those listed below:

Substituents for aliphatic, heteroaliphatic, cycloaliphatic and/or heterocycloaliphatic moieties can be one or more of a variety of groups selected from, but not limited to, aliphatic, aryl, alkyl, alkenyl, alkynyl, cycloalkyl, cycloalkenyl, cycloalkynyl, heteroaryl, heteroaliphatic, heteroalkyl, heterocyclic, —OR', oxo, =NR', =N—OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$. R', R", R'", and R"" each independently refer to hydrogen, aliphatic, heteroaliphatic, cycloaliphatic, heterocycloaliphatic, aryl or heteroaryl groups. In some embodiments, R', R", R'", and R"" can independently refer to aliphatic, alkyl, alkenyl, alkynyl, cycloalkyl, cycloalkenyl, cycloalkynyl, heteroaliphatic, or heterocyclic groups. When a compound includes more than one R', R", R'", or R"" group, for example, each of the R', R", R'", or R"" groups can be independently selected relative to the remaining R', R", R'", and R"" group(s). In some embodiments, when R' and R" are attached to the same atom, such as a nitrogen atom, they can be combined to form a cyclic structure, such as a 3-, 4-, 5-, 6-, or 7-membered heterocyclic ring.

Substituents for aryl and heteroaryl groups may be selected from, for example: aliphatic, aryl, alkyl, alkenyl, alkynyl, cycloalkyl, cycloalkenyl, cycloalkynyl, heteroalkyl, heteroaliphatic, heterocyclic, —OR', —NR'R", —SR', halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl; and where R', R", R'", and R"" are independently refer to hydrogen, aliphatic, heteroaliphatic, cycloaliphatic, heterocycloaliphatic, aryl or heteroaryl groups. In some embodiments, R', R", R'", and R"" can independently refer to aliphatic, alkyl, alkenyl, alkynyl, cycloalkyl, cycloalkenyl, cycloalkynyl, heteroaliphatic, or heterocyclic groups. When a compound includes more than one R', R", R'", or R"" group, for example, each of the R', R", R'", or R"" groups can be independently selected relative to the remaining R', R", R'", and R"" group(s). In some embodiments, when R' and R" are attached to the same atom, such as a nitrogen atom, they can be combined to form a cyclic structure, such as a 3-, 4-, 5-, 6-, or 7-membered heterocyclic ring.

Two or more substituents may optionally be joined to form aryl, heteroaryl, cycloaliphatic, or heterocycloaliphatic groups. Such ring-forming substituents are typically, though not necessarily, attached to a cyclic base structure. In some embodiments, the ring-forming substituents are attached to adjacent members of the base structure. For example, two ring-forming substituents can be attached to adjacent atoms of a cyclic base structure to create a fused ring structure. In other embodiments, the ring-forming substituents can be attached to a single atom of the base structure to create a spirocyclic structure. In yet another embodiment, the ring-forming substituents are attached to non-adjacent atoms of the base structure.

In one embodiment, a group that is substituted has 1 substituent, 2 substituents, 3 substituents, or 4 substituents.

The above definitions and the following general formulas are not intended to include impermissible substitution patterns (e.g., methyl substituted with 5 fluoro groups). Such impermissible substitution patterns are easily recognized by a person having ordinary skill in the art.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

Unless otherwise stated, structures depicted herein are also meant to include all stereochemical forms of the structure; such as the R and S configurations for each asymmetric center, the m and p configurations for each biaryl ring system, and E and Z configurations for olefins. Therefore, single stereochemical isomers, as well as enantiomeric, diastereomeric, and atropisomeric mixtures of the present compounds are within the scope of the disclosure, as well as racemic mixtures.

As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms. In cases of limited rotation, e.g. around the amide bond or between two directly attached rings such as a phenyl and pyridyl ring, atropisomers are also possible and are also specifically included in the compounds of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon, are within the scope of this disclosure.

The compounds of the present disclosure may also contain unnatural proportions of atomic isotopes at one or more of atoms that constitute such compounds. For example, the compounds may be radiolabeled with radioactive isotopes, such as, for example, tritium ($^3$H), iodine-125 ($^{125}$I), N-15 ($^{15}$N), or carbon-14 ($^{14}$C). All isotopic variations of the compounds of the present disclosure, whether radioactive or not, are encompassed within the scope of the present disclosure.

The term "alkyl," means, unless otherwise stated, a straight (i.e., unbranched), branched or cyclic saturated hydrocarbon chain (cycloalkyl), or combination thereof, and can include di- and multivalent moieties, having the number of carbon atoms designated (for example, C$_1$-C$_{10}$ includes alkyl groups comprising one to ten carbons). Examples of alkyl groups include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An "alkoxy" group is an alkyl group attached to the remainder of the molecule via an oxygen linker.

The term "aliphatic" refers to a substantially hydrocarbon-based compound, or a radical thereof (e.g., $C_6H_{13}$, for a hexane radical), including alkanes, alkenes, alkynes, including cyclic versions thereof, such as alkyl, alkenyl, alkynyl, cycloalkyl, cycloalkenyl, and cycloalkynyl, and further including straight- and branched-chain arrangements, and all stereo and position isomers as well. Unless expressly stated otherwise, an aliphatic group contains from one to at least twenty-five carbon atoms; for example, from one to fifteen, from one to ten, from one to six, or from one to four carbon atoms. The term "lower aliphatic" refers to an aliphatic group comprising from one to ten carbon atoms. An aliphatic chain may be substituted or unsubstituted. Unless expressly referred to as an "unsubstituted aliphatic," an aliphatic group can either be unsubstituted or substituted. An aliphatic group can be substituted with one or more substituents (up to two substituents for each methylene [—$CH_2$—] carbon in an aliphatic chain, or up to one substituent for each carbon of a —C═C— double bond in an aliphatic chain, or up to one substituent for a carbon of a terminal methine group).

The term "alkenyl" refers to straight chain or branched hydrocarbyl groups having from 2 to 10 carbon atoms, and in some embodiments 2 to 8 carbon atoms, and having at least 1 double bond. Such groups are exemplified, for example, bi-vinyl, allyl, and but-3-en-1-yl. Included within this term are the cis and trans isomers or mixtures of these isomers, unless otherwise specified. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), and the higher homologs and isomers. A person of ordinary skill in the art will understand that the olefin can be at any allowable position in an alkenyl chain. The term "cycloalkenyl" refers to a cyclic moiety derived from an alkenyl.

The term "alkynyl," by itself or as part of another substituent, refers to straight chain or branched hydrocarbyl groups having from 2 to 10 carbon atoms, and in some embodiments 2 to 8 carbon atoms, and having at least 1 site of triple bond unsaturation. Such groups are exemplified, for example, by ethynyl, 1-propynyl and 2-propynyl. The term "cycloalkynyl" refers to a cyclic moiety derived from an alkynyl. Example alkynyl groups include ethynyl, 1- and 3-propynyl, 3-butynyl, and higher homologs and isomers.

The term "heteroaliphatic" refers to an aliphatic compound or group having at least one heteroatom, i.e., one or more carbon atoms has been replaced with an atom having at least one lone pair of electrons, typically nitrogen, oxygen, phosphorus, silicon, or sulfur. Heteroaliphatic compounds or groups may be substituted or unsubstituted, branched or unbranched, cyclic or acyclic, and include "heteroalicyclyl" or "heterocycloaliphatic" groups. Examples of heteroalicyclyl groups include morpholine and piperidine.

The term "heteroalkyl," by itself or in combination with another term, means, unless otherwise stated, a stable straight, branched or cyclic chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —Si($CH_3$)$_3$. Up to two heteroatoms may be consecutive, such as, for example, —$CH_2$—NH—$OCH_3$.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "heterocyclyl," "heterocyclo," "heterocyclic" and "heterocycle" refer to aromatic and non-aromatic ring systems, and more specifically refer to a stable three- to fifteen-membered ring moiety comprising carbon atoms and at least one, such as from one to five heteroatoms. The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and the nitrogen, phosphorus, carbon, silicon or sulfur atoms in the heterocyclyl moiety can be optionally oxidized to various oxidation states. For convenience, nitrogens, particularly but not exclusively, those defined as annular aromatic nitrogens, are meant to include their corresponding N-oxide form, although not explicitly defined as such in a particular example. Thus, for a compound having, for example, a pyridyl ring; the corresponding pyridyl-N-oxide is included as another compound of the invention, unless expressly excluded by context. In addition, annular nitrogen atoms can be optionally quaternized. Heterocycle includes heteroaryl moieties, and heteroalicyclyl or heterocycloaliphatic moieties, which are heterocyclyl rings which are partially or fully saturated. Thus a term such as "heterocyclylalkyl" includes heteroalicyclylalkyls and heteroarylalkyls. Examples of heterocyclyl groups include, but are not limited to, azetidinyl, oxetanyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "hydroxyl" refers to the group —OH.

The term "amino," refers to a chemical functional group —N($R^a$)$R^b$ where $R^a$ and $R^b$ are independently hydrogen, aliphatic, alkyl, heteroalkyl, haloalkyl, aliphatic, heteroaliphatic, aryl (such as phenyl), heteroaryl, or other functionality, or where $R^a$ and $R^b$ are optionally joined together with the nitrogen bound thereto to form a cycloamino group such as a heterocyclic or heteroaryl group comprising at least one ring nitrogen. Exemplary cycloamino groups include, but are not limited to, pyrrolidine, pyrrole, imidazole, triazole, tetrazole, piperidine, triazinane, piperazine, morpholine, azepane, diazepane, azocane, diazocane, azonane or azecane. A "primary amino" group is —$NH_2$.

The term "aminocarbonyl" refers to a chemical functional group —C(O)-amino, where amino is as defined herein. A primary aminocarbonyl is —$CONH_2$.

The term "cyano" refers to the chemical functional group —CN.

The term "carboxyl," "carboxylic acid" or "carboxy" refers to the chemical functional group —$CO_2H$.

The term "carboxyl ester," "carboxylic acid ester," or "carboxy ester" refers to the chemical functional group —$CO_2R$ where R is aliphatic, alkyl, heteroalkyl, haloalkyl, aliphatic, heteroaliphatic, aryl (such as phenyl), heteroaryl, or other functionality. In particular embodiments, R is aryl or heteroaryl.

The term "aminosulfonyl" refers to a chemical function group —$SO_2$-amino, where amino is as defined herein. A primary aminosulfonyl is —$SO_2NH_2$.

The term "acyl" means, unless otherwise stated, —C(O)R where R is aliphatic, alkyl, cycloalkyl, heteroalkyl, heteroaliphatic, heterocycloalkyl, aryl, or heteroaryl.

The term "aryl" or "Ar" refers to a monovalent aromatic carbocyclic group of from 6 to 15 carbon atoms having a single ring (e.g., phenyl) or multiple condensed rings (e.g., naphthyl or anthryl) in which at least one of the condensed rings is aromatic (e.g., 2-benzoxazolinone, 2H-1,4-benzoxazin-3(4H)-one-7-yl, 9,10-dihydrophenanthrene, and the like), provided that the point of attachment is through an atom of the aromatic aryl group. Unless otherwise specified, the aryl group may be optionally substituted. Preferred aryl groups include phenyl and naphthyl.

The term "heteroaryl" refers to an aromatic group having from 1 to 15 carbon atoms and at least one, and more typically 1 to 4, heteroatoms selected from oxygen, nitrogen or sulfur within the ring. Unless otherwise specified, the heteroaryl group may be optionally substituted. Such heteroaryl groups can have a single ring (e.g., pyridinyl, imidazolyl or furyl) or multiple condensed rings (e.g., indolizinyl, quinolinyl, benzimidazolyl, benzopyrazolyl or benzothienyl), wherein at least one of the condensed rings is aromatic and may or may not contain a heteroatom, provided that the point of attachment is through an atom of an aromatic ring. In one embodiment, the nitrogen and/or sulfur ring atom(s) of the heteroaryl group are optionally oxidized to provide N-oxide (N→O), sulfinyl, or sulfonyl moieties. Preferred heteroaryls include pyridinyl, pyrrolyl, indolyl, thienyl, benzopyrazolyl and furanyl.

The term "oxo," as used herein, means an oxygen that is double bonded to a carbon atom.

The term "sulfonyl" refers to the group —$SO_2$—, and includes —$SO_2$-aliphatic, —$SO_2$-aryl, —$SO_2$-heteroaryl, or —$SO_2$-heterocyclic, wherein aliphatic, aryl, heteroaryl, and heterocyclic are as defined herein. Sulfonyl includes groups such as methyl-$SO_2$—, phenyl-$SO_2$—, and 4-methylphenyl-$SO_2$—.

The term "bioisostere" refers to chemical substituents or groups with similar physical or chemical properties which produce broadly similar biological properties to another chemical compound. The physical and chemical properties may include, but are not limited to, molecular shape, volume and/or electron distribution. For example, in drug design, one bioisostere may be exchanged for another to enhance the desired biological or physical properties of a compound without making significant changes in chemical structure. In some examples, bioisosteres may be used to reduce toxicity, change bioavailability, modify the activity, and/or alter the metabolism of a compound.

The term "pharmaceutically acceptable salt" refers to pharmaceutically acceptable salts of a compound that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compounds form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

II. Compounds

Disclosed herein are embodiments of a compound having a formula I

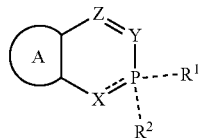

I or a pharmaceutically acceptable salt thereof.

With reference to formula I, ring A is aryl, heteroaryl, cycloaliphatic or heterocyclic; X is O, S, SO, SO$_2$, or NR$^3$; Y is N or CR$^4$; Z is CR$^4$ or N; R$^1$ is —OH, aliphatic, aryl, heteroaryl, heterocyclic, heteroaliphatic, —O-aliphatic, —O-aryl, —O-heteroaryl, —O-heterocyclic, or —O-heteroaliphatic; R$^2$ is oxo (=O), =S, =Se, —OH, aliphatic, aryl, heteroaryl, heterocyclic, heteroaliphatic, —O-aliphatic, —O-aryl, —O-heteroaryl, —O-heterocyclic, or —O-heteroaliphatic; R$^3$ is H, aliphatic, heteroaliphatic, aryl, heterocyclic, heteroaryl, acyl, carboxyl ester, or a lone pair of electrons; and each R$^4$ independently is H, aliphatic, heteroaliphatic, aryl, heterocyclic, heteroaryl, halo, CN, NO$_2$, sulfonyl, amino, carboxyl, carboxyl ester, aminosulfonyl, or aminocarbonyl.

In certain embodiments, R$^1$ is —OH, alkyl, alkenyl, alkynyl, cycloalkyl, cycloalkenyl, cycloalkynyl, aryl, heteroaryl, heterocyclic, heterocycloaliphatic, heteroalkyl, heterocycloalkyl, —O-alkyl, —O-alkenyl, —O-alkynyl, —O-cycloalkyl, —O-cycloalkenyl, —O-cycloalkynyl, —O-aryl, —O— heteroaryl, —O-heterocyclic, —O-heterocycloaliphatic, —O-heteroalkyl or —O-heterocycloalkyl. R$^2$ may be oxo, —OH, alkyl, alkenyl, alkynyl, cycloalkyl, cycloalkenyl, cycloalkynyl, aryl, heteroaryl, heterocyclic, heterocycloaliphatic, heteroalkyl, heterocycloalkyl, —O-alkyl, —O— alkenyl, —O-alkynyl, —O-cycloalkyl, —O-cycloalkenyl, —O-cycloalkynyl, —O-aryl, —O-heteroaryl, —O-heterocyclic, —O-heterocycloaliphatic, —O-heteroalkyl or —O-heterocycloalkyl. R$^3$ may be H, alkyl, alkenyl, alkynyl, cycloalkyl, cycloalkenyl, cycloalkynyl, aryl, -alkylaryl, heteroaryl, heterocyclic, heterocycloaliphatic, heteroalkyl, heterocycloalkyl, carboxyl ester, or a lone pair of electrons. In some embodiments, R$^3$ is H, methyl, ethyl, n-propyl, i-propyl, cyclopropyl, benzyl, acetyl, or formyl. And each R$^4$ independently may be H, alkyl, alkenyl, alkynyl, haloalkyl such as CF$_3$, cycloalkyl, cycloalkenyl, cycloalkynyl, aryl, heteroaryl, heterocyclic, heterocycloaliphatic, heteroalkyl, heterocycloalkyl, halo, CN, NO$_2$, sulfonyl, amino, carboxyl, carboxyl ester, aminosulfonyl, or aminocarbonyl. In certain embodiments, Z is CH or N.

In some embodiments when Y is CR$^4$, including certain specific embodiments where X is O and Y is CR$^4$, R$^4$ is not CO$_2$-alkyl. In other embodiments, R$^4$ is selected from H, alkyl, alkenyl, alkynyl, haloalkyl, cycloalkyl, cycloalkenyl, cycloalkynyl, aryl, heteroaryl, heterocyclic, heterocycloaliphatic, heteroalkyl, heterocycloalkyl, halo, CN, NO$_2$, sulfonyl, amino, carboxyl, aminosulfonyl, aminocarbonyl or a carboxyl ester having a formula —CO$_2$R where R is aryl or heteroaryl, particularly phenyl.

In some embodiments, the compound has a structure

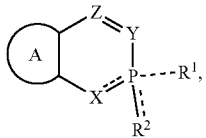

where A, X, Y, Z, R$^1$ and R$^2$ are as previously defined.

In some embodiments where X is O, S, SO or SO$_2$, and R$^2$ is oxo, and the compound has a formula II

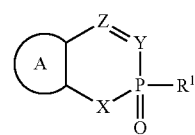

II or a pharmaceutically acceptable salt thereof, where ring A, Y, Z, and R$^1$ are as previously defined for formula I.

In other embodiments of formula I, X is NR$^3$ and the compound has a formula selected from formulas III, IV or V

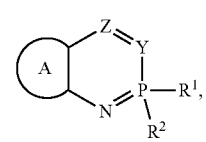

III

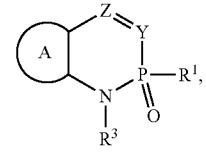

IV

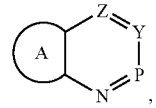

V or a pharmaceutically acceptable salt thereof.

With respect to these formulas, ring A, Y, Z, R$^1$ and R$^3$, if present, are as previously defined for formula I, and R$^2$, if present, is —OH, aliphatic, aryl, heteroaryl, heterocyclic, heteroaliphatic, —O-aliphatic, —O-aryl, —O-heteroaryl, —O-heterocyclic, or —O-heteroaliphatic. In some embodiments, R$^2$ is —OH, alkyl, alkenyl, alkynyl, cycloalkyl, cycloalkenyl, cycloalkynyl, aryl, heteroaryl, heterocyclic, heterocycloaliphatic, heteroalkyl, heterocycloalkyl, —O-alkyl, —O— alkenyl, —O-alkynyl, —O-cycloalkyl, —O-cycloalkenyl, —O-cycloalkynyl, —O-aryl, —O-heteroaryl, —O-heterocyclic, —O-heterocycloaliphatic, —O-heteroalkyl or —O-heterocycloalkyl.

In some embodiments of formulas I-V, ring A is aryl or heteroaryl, and may be a 5-membered aryl, 5-membered heteroaryl, 6-membered aryl or 6-membered heteroaryl. Exemplary ring A moieties include, but not limited to, phenyl, naphthyl, benzodioxinyl, benzodioxolyl, quinolinyl, pyridinyl, pyrimidinyl, pyrazinyl, thienyl, furanyl, imidazolyl, pyrazolyl, oxazolyl, thiazolyl, triazolyl, oxadiazolyl or thiadiazolyl. In certain embodiments, ring A is phenyl, naphthyl, or thienyl.

In certain embodiments of formulas I-V, Z is CH and Y is $CR^4$, and in particular embodiments, Y is not CH, and/or each $R^4$ independently may be selected from aliphatic, heteroaliphatic, aryl, heterocyclic, heteroaryl, halo, CN, $NO_2$, sulfonyl, amino, carboxyl, carboxyl ester, aminosulfonyl, or aminocarbonyl.

With respect to formulas I-IV, $R^1$ and $R^2$, if present, independently may be —O-aryl; aliphatic such as alkyl, alkenyl, alkynyl, cycloalkenyl or cycloalkynyl; aryl, such as phenyl; heteroaryl, such as thienyl; heterocyclic such as heterocycloaliphatic or heterocycloalkyl; or heteroaliphatic, such as heteroalkyl. In particular embodiments, $R^1$ and $R^2$, if present, are —O— phenyl.

And in some embodiments of formula I, II and IV, $R^3$ is H, and in other embodiments, $R^3$ is alkyl, acyl or carboxyl ester. $R^3$ may be a protecting group, such as $C(O)CH_3$, benzyl, tert-butoxycarbonyl (BOC), fluorenylmethyloxycarbonyl (FMOC) or carboxybenzyl (CBZ).

In some embodiments of formulas I-V, ring A is phenyl, leading to compounds having a formula selected from

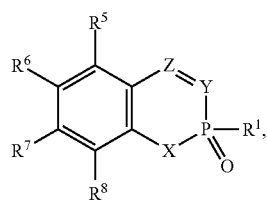

VI

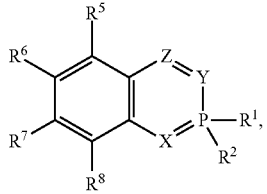

VII

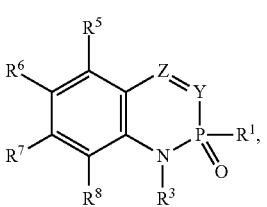

VIII

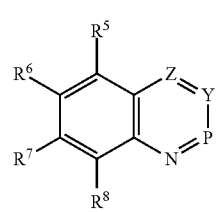

IX or a pharmaceutically acceptable salt thereof.

With respect to formulas VI-IX, X is as defined for formula II; Y, Z, $R^1$, $R^2$ and $R^3$, if present, are as defined for formulas I-V; and $R^5$, $R^6$, $R^7$ and $R^8$ independently are H, aliphatic, haloalkyl, heteroaliphatic, aryl, heterocyclic, heteroaryl, —O-aliphatic, —O-heteroaliphatic, —O-heterocyclic, —O-heteroaryl, —O-aryl, halo, OH, CN, $NO_2$, sulfonyl, amino, carboxyl, carboxyl ester, aminosulfonyl, or aminocarbonyl or any two adjacent groups together form an aliphatic, heterocyclic, aryl or heteroaryl ring. In some embodiments, $R^5$, $R^6$, $R^7$ and $R^8$ independently are H, alkyl, alkenyl, alkynyl, cycloalkyl, cycloalkenyl, cycloalkynyl, haloalkyl such as $CF_3$, aryl, heteroaryl, heterocyclic, heterocycloaliphatic, heteroalkyl, heterocycloalkyl, —O-alkyl, —O— alkenyl, —O-alkynyl, —O-heteroaliphatic, —O-heterocyclic, —O-heteroaryl, —O-aryl, halo, CN, $NO_2$, sulfonyl, amino, carboxyl, carboxyl ester, aminosulfonyl, or aminocarbonyl or any two adjacent groups together form an aliphatic, heterocyclic, aryl or heteroaryl ring.

In some embodiments of formulas VI-IX, Z is CH and/or Y is $CR^4$.

Compounds according to formula VI may have a formula selected from

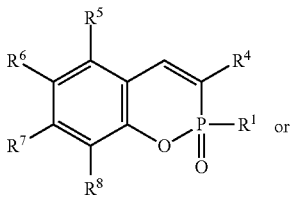

X

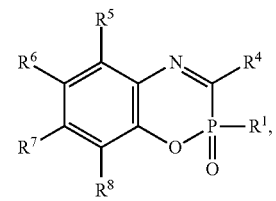

XI or a pharmaceutically acceptable salt thereof.

With respect to formulas X and XI, $R^1$, $R^4$, $R^5$, $R^6$, $R^7$ and $R^8$ are as previously defined.

Compounds according to formula VII may have a formula XII

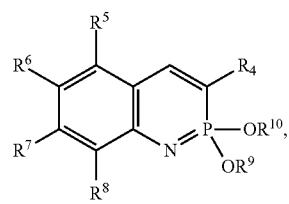

XII or a pharmaceutically acceptable salt thereof.

With respect to formula XII, $R^4$, $R^5$, $R^6$, $R^7$ and $R^8$ are as previously defined, and $R^9$ and $R^{10}$ independently are aryl; aliphatic, such as alkyl, alkenyl, alkynyl, cycloalkyl, cycloalkenyl, or cycloalkynyl; heteroaryl; heterocyclic; heterocycloaliphatic; heteroalkyl; or heterocycloalkyl. In some embodiments, $R^9$ and $R^{10}$ independently are phenyl, pyridyl, methyl, ethyl, propyl, cyclopropyl, isopropyl, butyl, isobutyl or tert-butyl. In certain embodiments, both $R^9$ and $R^{10}$ are phenyl.

Compounds according to formula VIII may have a formula XIII

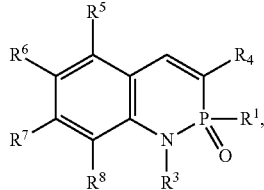

XIII or a pharmaceutically acceptable salt thereof.

With respect to formula XIII, $R^1$, $R^3$, $R^4$, $R^5$, $R^6$, $R^7$ and $R^8$ are as previously defined. In some embodiments, $R^1$ is —O-phenyl, methoxy, ethoxy, propoxy, cyclopropoxy, isopropoxy, butoxy, isobutoxy, tert-butoxy, phenyl, pyridyl, methyl, ethyl, propyl, cyclopropyl, isopropyl, n-butyl, isobutyl, sec-butyl, or tert-butyl. In certain embodiments, $R^1$ is —O-phenyl. $R^3$ may be H, alkyl, -alkylaryl, or acyl, and in certain embodiments, $R^3$ is H, methyl, ethyl, isopropyl, benzyl, or acetyl.

Compounds according to formula IX may have a formula XIV

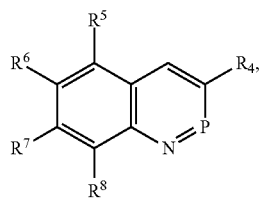

XIV or a pharmaceutically acceptable salt thereof.

With respect to formula XIV, $R^4$, $R^5$, $R^6$, $R^7$ and $R^8$ are as previously defined.

With respect to any of formulas VI-XIV, $R^5$, $R^6$, $R^7$ and $R^8$ independently are H, aryl, alkyl, heteroaryl, amino, $NO_2$, CN, $CF_3$, OH, —O-alkyl, sulfonyl, carboxyl, carboxyl ester, or two adjacent groups together form an aryl, heteroaryl, heterocyclic, or cycloaliphatic ring. In certain embodiments, any two adjacent groups from $R^5$, $R^6$, $R^7$ and $R^8$ together with the phenyl ring to which they are attached, form a naphthalene, quinoline, benzodioxole, benzodioxine, dihydrobenzoxazine, tetrahydroquinoxaline, tetrahydronaphthalene, benzoxazole, benzthiazole, or benzimidazole ring system.

Alternatively, or additionally, $R^5$, $R^6$, $R^7$ or $R^8$ independently may comprise a moiety according to one of formulas VI-XIV. In some embodiments, the compound is a dimer, trimer or tetramer, that is the compound comprises two, three or four moieties each having a structure according to one of formulas VI-XIV. The moieties are connected to each other through a linker. The linker can be any suitable linker, including, but to limited to, a bond; an aryl moiety, such as phenyl; an aliphatic moiety, such as alkyl, alkenyl, alkynyl, cycloalkyl, cycloalkenyl, or cycloalkynyl; a heteroaliphatic; a heteroaryl moiety; a heterocyclic moiety; a heterocycloaliphatic moiety; a heteroalkyl moiety; or a heterocycloalkyl moiety. In some embodiments, the compound is a dimer comprising two moieties according to formula XII or formula XIII. In certain embodiments, the compound has a formula selected from formula XV or formula XVI:

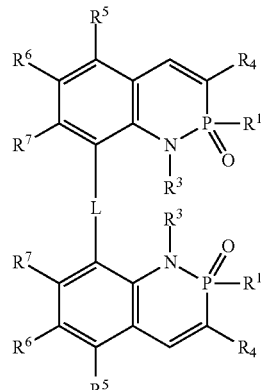

XV

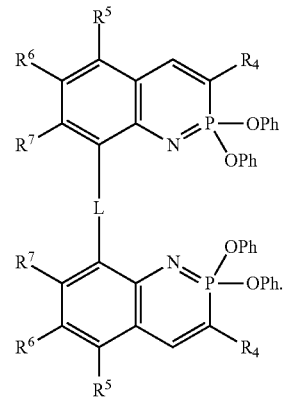

XVI

With respect to formulas XV and XVI, each $R^1$ independently is a defined as for formula I, each $R^4$, $R^5$, $R^6$, and $R^7$ independently is as previously defined for formulas XII and XIII, and L is a bond, aliphatic, aryl, heteroaryl, heteroaliphatic, or heterocyclic. In certain embodiments, L is phenyl, and may be a 1,2-, 1,3-, or 1,4-substituted phenyl.

In other embodiments of formulas I-V, ring A is thienyl. In certain embodiments, the compound has a formula selected from

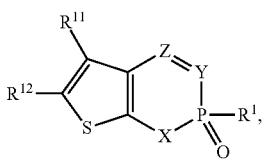

XIV

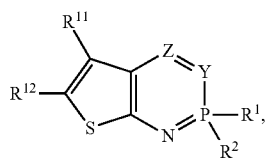

XV

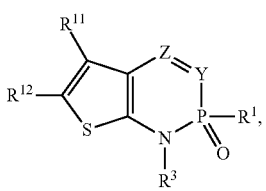

XVI

-continued

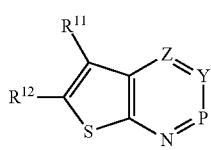
XVII or a pharmaceutically acceptable salt thereof.

With respect to formulas VI-IX, X is as defined for formula II; Y, Z, $R^1$, $R^2$ and $R^3$, if present, are as defined for formulas I-V; and $R^{11}$ and $R^{12}$ independently are H, aliphatic, haloalkyl, heteroaliphatic, aryl, heterocyclic, heteroaryl, —O-aliphatic, —O-heteroaliphatic, —O-heterocyclic, —O-heteroaryl, —O-aryl, halo, OH, CN, $NO_2$, sulfonyl, amino, carboxyl, carboxyl ester, aminosulfonyl, or aminocarbonyl or any two adjacent groups together form an aliphatic, heterocyclic, aryl or heteroaryl ring. In some embodiments, $R^{11}$ and $R^{12}$ independently are H, alkyl, alkenyl, alkynyl, cycloalkyl, cycloalkenyl, cycloalkynyl, haloalkyl such as $CF_3$, aryl, heteroaryl, heterocyclic, heterocycloaliphatic, heteroalkyl, heterocycloalkyl, —O-alkyl, —O—alkenyl, —O-alkynyl, —O-heteroaliphatic, —O-heterocyclic, —O-heteroaryl, —O-aryl, halo, CN, $NO_2$, sulfonyl, amino, carboxyl, carboxyl ester, aminosulfonyl, or aminocarbonyl or any two adjacent groups together form an aliphatic, heterocyclic, aryl or heteroaryl ring.

In some embodiments of formulas XIV-XVII, Z is CH and/or Y is $CR^4$.

In certain embodiments of formulas XIV-XVII, the compound has a formula selected from

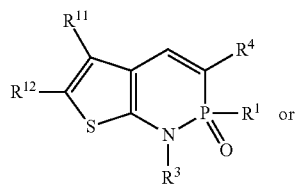
XVIII

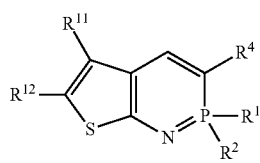
XIX where $R^1$, $R^2$, $R^3$, $R^{11}$ and $R^{12}$ are as defined for formulas XIV-XVII, and $R^4$ is as defined for formula I.

With respect to any of formulas VI-XIX, each $R^4$ independently is pyridyl; phenyl; phenyl substituted with one or more substituents selected from CN, $CO_2$alkyl such as $CO_2Et$, —O-alkyl such as methoxy, haloalkyl such as $CF_3$; alkyl or cycloalkyl, such as methyl, ethyl, n-propyl, isopropyl, cyclopropyl, n-butyl, isobutyl, sec-butyl, tert-butyl, cyclobutyl, n-pentyl or cyclopentyl.

Some exemplary compounds according to formula XII include:

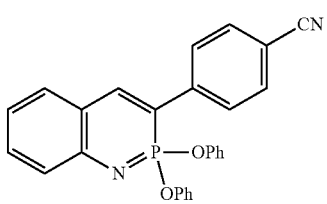
I-1

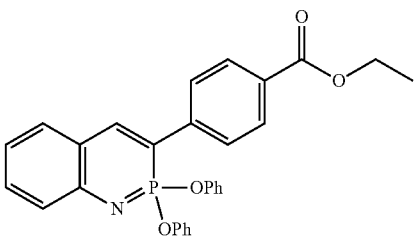
I-2

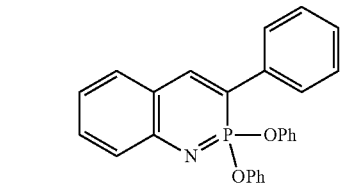
I-3

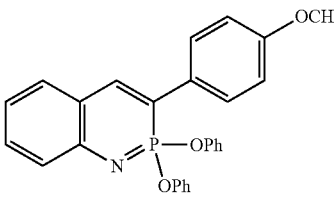
I-4

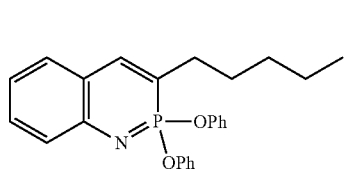
I-5

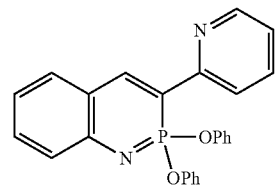
I-6

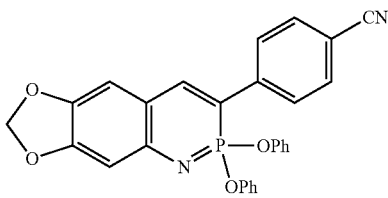
I-7

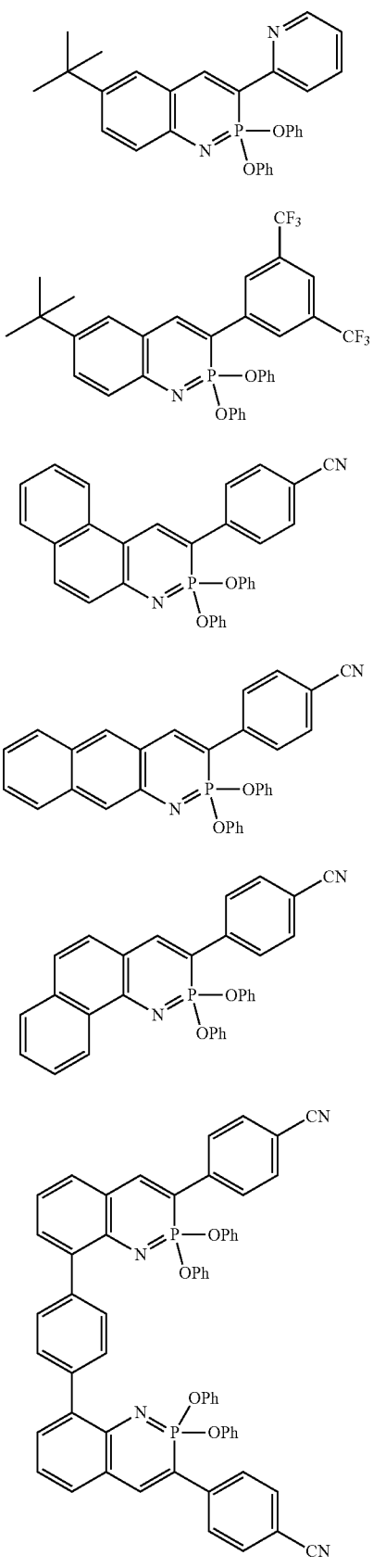
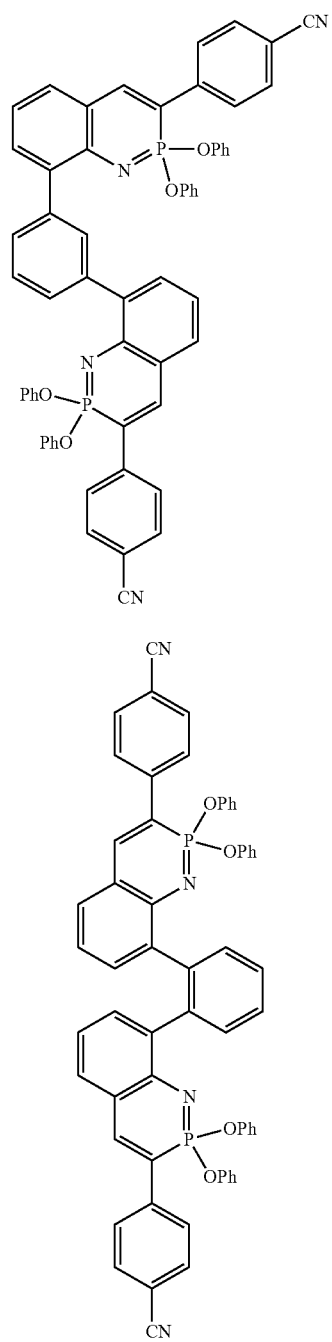
Some exemplary compounds according to formula XIII include:
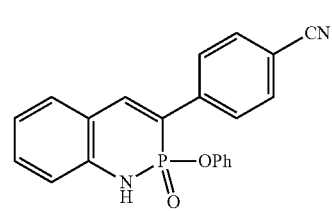

-continued

II-2

II-3

II-4

II-5

II-6

II-7

II-8

II-9

II-10

II-11

II-12

II-13

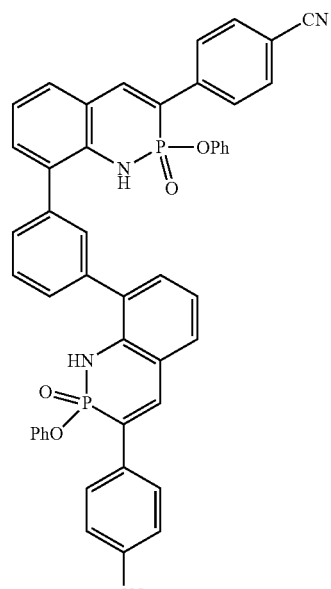
II-14
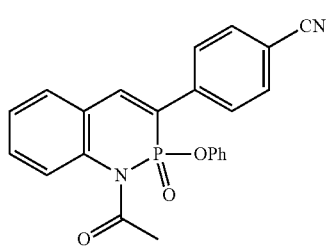
II-17
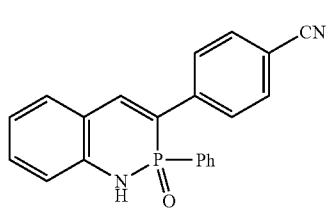
II-18
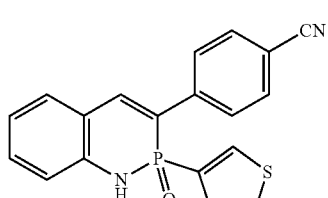
II-19
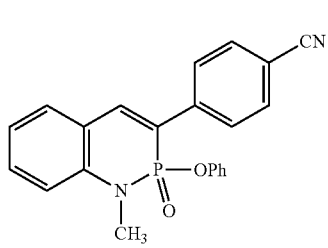
II-20
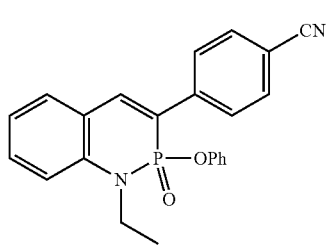
II-21
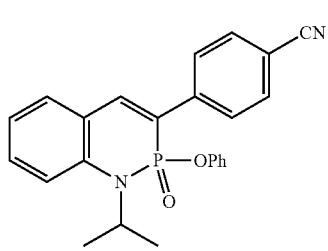
II-22
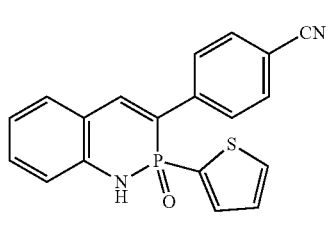
II-23
II-15
II-16

Some additional exemplary compounds include:

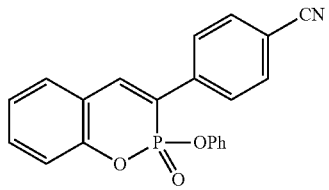

III-1

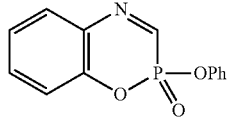

III-2

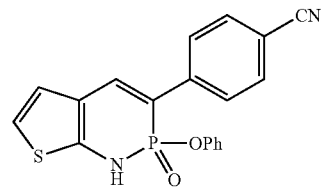

III-3

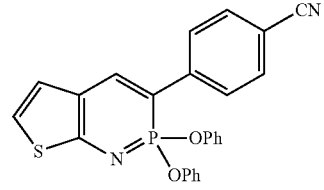

III-4

Some exemplary embodiments include:
4-(2,2-diphenoxy-2-λ$^5$-benzo[e][1,2]azaphosphinin-3-yl)benzonitrile;
ethyl 4-(2,2-diphenoxy-2-λ$^5$-benzo[e][1,2]azaphosphinin-3-yl)benzoate;
2,2-diphenoxy-3-phenyl-2-λ$^5$-benzo[e][1,2]azaphosphinine;
3-(4-methoxyphenyl)-2,2-diphenoxy-2-λ$^5$-benzo[e][1,2]azaphosphinine;
3-pentyl-2,2-diphenoxy-2-λ$^5$-benzo[e][1,2]azaphosphinine;
2,2-diphenoxy-3-(pyridin-2-yl)-2-λ$^5$-benzo[e][1,2]azaphosphinine;
4-(2,2-diphenoxy-2-λ$^5$-[1,3]dioxolo[4',5':4,5]benzo[1,2-e][1,2]azaphosphinin-3-yl)benzonitrile;
6-(tert-butyl)-2,2-diphenoxy-3-(pyridin-2-yl)-2-λ$^5$-benzo[e][1,2]azaphosphinine;
3-(3,5-bis(trifluoromethyl)phenyl)-6-(tert-butyl)-2,2-diphenoxy-2-λ$^5$-benzo[e][1,2]azaphosphinine;
4-(3,3-diphenoxy-3-λ$^5$-naphtho[1,2-e][1,2]azaphosphinin-2-yl)benzonitrile;
4-(2,2-diphenoxy-2-λ$^5$-naphtho[2,3-e][1,2]azaphosphinin-3-yl)benzonitrile;
4-(2,2-diphenoxy-2-λ$^5$-naphtho[2,1-e][1,2]azaphosphinin-3-yl)benzonitrile;
4,4'-(1,4-phenylenebis(2,2-diphenoxy-2λ$^5$-benzo[e][1,2]azaphosphinine-8,3-diyl))dibenzonitrile;
4,4'-(1,3-phenylenebis(2,2-diphenoxy-2λ$^5$-benzo[e][1,2]azaphosphinine-8,3-diyl))dibenzonitrile; or
4,4'-(1,2-phenylenebis(2,2-diphenoxy-2'$^5$-benzo[e][1,2]azaphosphinine-8,3-diyl))dibenzonitrile.
Other exemplary embodiments include:
4-(2-oxido-2-phenoxy-1H-benzo[e][1,2]azaphosphinin-3-yl)benzonitrile;
ethyl 4-(2-oxido-2-phenoxy-1H-benzo[e][1,2]azaphosphinin-3-yl)benzoate;
2-phenoxy-3-phenyl-1H-benzo[e][1,2]azaphosphinine 2-oxide;
3-(4-methoxyphenyl)-2-phenoxy-1H-benzo[e][1,2]azaphosphinine 2-oxide;
3-pentyl-2-phenoxy-1H-benzo[e][1,2]azaphosphinine 2-oxide;
2-phenoxy-3-(pyridin-2-yl)-1H-benzo[e][1,2]azaphosphinine 2-oxide;
4-(2-oxido-2-phenoxy-1H-[1,3]dioxolo[4',5':4,5]benzo[1,2-e][1,2]azaphosphinin-3-yl)benzonitrile;
6-(tert-butyl)-2-phenoxy-3-(pyridin-2-yl)-1H-benzo[e][1,2]azaphosphinine 2-oxide;
3-(3,5-bis(trifluoromethyl)phenyl)-6-(tert-butyl)-2-phenoxy-1H-benzo[e][1,2]azaphosphinine 2-oxide;
4-(3-oxido-3-phenoxy-4H-naphtho[1,2-e][1,2]azaphosphinin-2-yl)benzonitrile;
4-(2-oxido-2-phenoxy-1H-naphtho[2,3-e][1,2]azaphosphinin-3-yl)benzonitrile;
4-(2-oxido-2-phenoxy-1H-naphtho[2,1-e][1,2]azaphosphinin-3-yl)benzonitrile;
4,4'-(1,4-phenylenebis(2-oxido-2-phenoxy-1H-benzo[e][1,2]azaphosphinine-8,3-diyl))dibenzonitrile;
4,4'-(1,3-phenylenebis(2-oxido-2-phenoxy-1H-benzo[e][1,2]azaphosphinine-8,3-diyl))dibenzonitrile;
4,4'-(1,2-phenylenebis(2-oxido-2-phenoxy-1H-benzo[e][1,2]azaphosphinine-8,3-diyl))dibenzonitrile;
4-(1-benzyl-2-oxido-2-phenoxy-1H-benzo[e][1,2]azaphosphinin-3-yl)benzonitrile;
4-(1-acetyl-2-oxido-2-phenoxy-1H-benzo[e][1,2]azaphosphinin-3-yl)benzonitrile;
4-(2-oxido-2-phenyl-1H-benzo[e][1,2]azaphosphinin-3-yl)benzonitrile;
4-(2-oxido-2-(thiophen-3-yl)-1H-benzo[e][1,2]azaphosphinin-3-yl)benzonitrile;
4-(1-methyl-2-oxido-2-phenoxy-1H-benzo[e][1,2]azaphosphinin-3-yl)benzonitrile;
4-(1-ethyl-2-oxido-2-phenoxy-1H-benzo[e][1,2]azaphosphinin-3-yl)benzonitrile;
4-(1-isopropyl-2-oxido-2-phenoxy-1H-benzo[e][1,2]azaphosphinin-3-yl)benzonitrile; or
4-(2-oxido-2-(thiophen-2-yl)-1H-benzo[e][1,2]azaphosphinin-3-yl)benzonitrile.
Additional exemplary compounds include:
4-(2-oxido-2-phenoxybenzo[e][1,2]oxaphosphinin-3-yl)benzonitrile;
2-phenoxybenzo[e][1,4,2]oxazaphosphinine 2-oxide;
4-(2-oxido-2-phenoxy-1H-thieno[3,2-e][1,2]azaphosphinin-3-yl)benzonitrile; or
4-(2,2-diphenoxy-2λ$^5$-thieno[3,2-e][1,2]azaphosphinin-3-yl)benzonitrile.

III. Method for Making the Compounds

Disclosed compounds can be prepared as exemplified below, and as will be understood by a person of ordinary skill in the art in organic synthesis. With reference to the following Schemes, each $R^a$ independently is aliphatic, haloalkyl, heteroaliphatic, aryl, heterocyclic, heteroaryl, —O-aliphatic, —O-heteroaliphatic, —O-heterocyclic, —O-heteroaryl, —O-aryl, halo, OH, CN, $NO_2$, sulfonyl, amino, carboxyl, carboxyl ester, aminosulfonyl, or aminocarbonyl or any two adjacent $R^a$s together form an aliphatic, heterocyclic, aryl or heteroaryl ring; $R^b$ is H, alkyl, alkenyl, alkynyl, haloalkyl such as $CF_3$, cycloalkyl, cycloalkenyl, cycloalkynyl, aryl, heteroaryl, heterocyclic, heterocycloaliphatic, heteroalkyl, heterocycloalkyl, halo, CN, $NO_2$, sulfonyl, amino, carboxyl, carboxyl ester, aminosulfonyl, or aminocarbonyl; and n is 0, 1, 2, 3 or 4.

An exemplary synthesis of certain disclosed compounds may be according to Scheme 1:

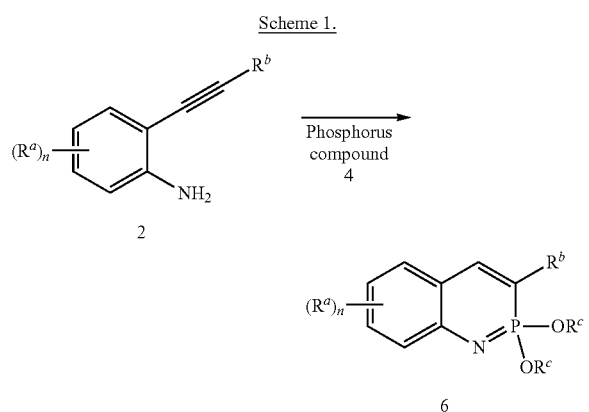

Scheme 1.

With respect to Scheme 1, alkynyl compound 2 is reacted with a phosphorus compound 4 to form compound 6 at a temperature suitable to facilitate the reaction. In some embodiments, phosphorus compound 4 is a tri-substituted phosphite, such as a triaryl phosphite, triheteroaryl phosphite or trialkyl phosphite. In certain embodiments, phosphorus compound 4 is triphenylphosphite. In other embodiments, phosphorus compound 4 is a disubstituted phosphorochloridite (ClP(R)(R')), such as a dialkyl phosphorochloridite, diaryl phosphorochloridite or diheteroaryl phosphorochloridite. A suitable temperature for the reaction is typically from greater than zero to at least 150 OC, such as from 50° C. to 150° C. or from 75° C. to 125° C., and in certain embodiments 100° C. The reaction is performed in a solvent suitable to facilitate the reaction, such as a non-protic solvent. Suitable solvents include, but are not limited to, pyridine. The reaction may be performed under an inert and/or dry atmosphere, such as under nitrogen or argon.

Certain other compounds may be synthesized according to Scheme 2:

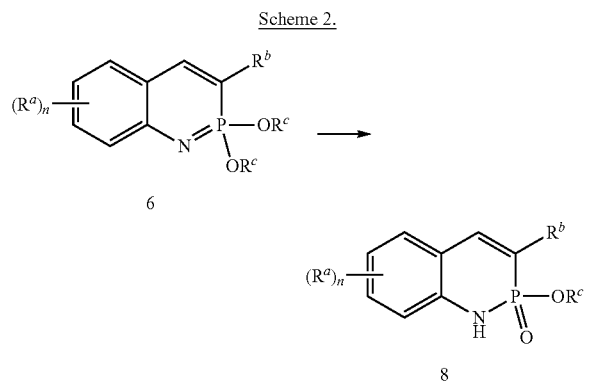

Scheme 2.

Compound 6 is reacted with water, at a temperature suitable to facilitate a reaction, to form compound 8. A suitable temperature is typically from 50° C. to 150° C., such as from 75° C. to 125° C., or from 90° C. to 105° C., and in certain embodiments, the temperature is 100° C. In some embodiments, compound 6 is isolated and then reacted with water to form compound 8. In other embodiments, compound 8 is formed in a one pot reaction from compounds 2 and 4 according to scheme 1, except that the reaction is performed under an ambient atmosphere and/or in the presence of water, rather than a dry atmosphere. In these embodiments, compound 6 forms in situ and is then converted to compound 8 without being isolated.

In some embodiments, compound 8 is hydrolysed by reaction with water, optionally in the presence of a base, to form compound 10 (Scheme 3).

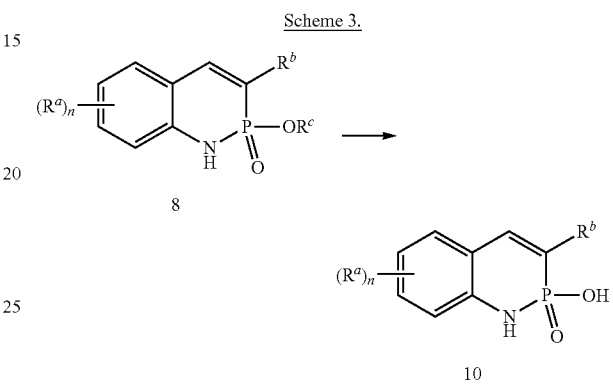

Scheme 3.

Compound 8 also may be trans-esterified to form compound 12, according to Scheme 4.

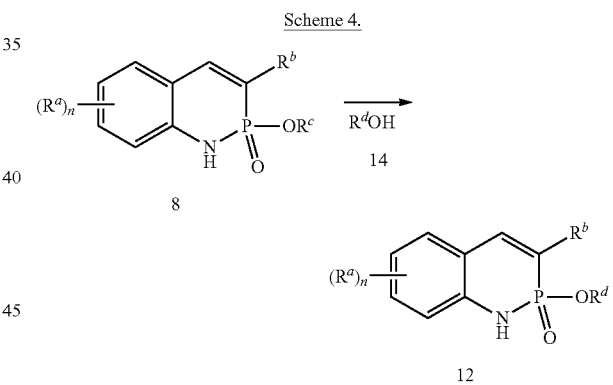

Scheme 4.

With reference to Scheme 4, compound 14 may be any suitable alcohol, including, but not limited to, an alkyl alcohol, such as methanol, ethanol, n-propanol, isopropanol, n-butanol or tert-butanol; an aromatic alcohol, such as a substituted phenol or naphthanol; a heteroaryl alcohol, such as a hydroxypyridine or hydroxythiophene; or a heteroaliphatic or heterocyclic alcohol, such as a polyethylene glycol (PEG) or hydroxy piperidine. The trans-esterification reaction may be performed in the presence of a catalyst, such as an acid or basic catalyst.

Suitable catalysts include, but are not limited to, sulfuric acid, para-toluene sulfonic acid (PTSA), HCl, sodium or potassium alkoxide and/or the sodium or potassium salt of compound 14. The trans-esterification reaction is performed in a suitable solvent. Suitable solvents include an excess of compound 14, an alcohol such as methanol or ethanol, or a non-protic solvent, such as toluene, DMF, chloroform, dichloromethane, acetonitrile, or any combination thereof.

In some embodiments, compound 8 is reacted with an organometallic reagent 16, such as a Grignard reagent, to form compound 18, according to Scheme 5.

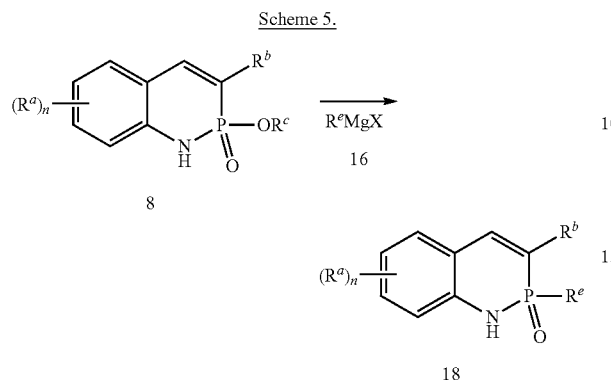

Scheme 5.

With respect to Scheme 5, $R^e$ is aryl, heteroaryl or aliphatic, typically alkyl, and X is a halogen, typically, Cl, Br or I. The reaction is performed in a suitable solvent, typically an aprotic solvent such as diethyl ether, THF, MTBE, hexanes, or a combination thereof.

Certain disclosed compounds that comprise an NH moiety in the ring, can be further reacted at the NH position. For example, compound 8 may be reacted with a suitable reagent 20 comprising a leaving group to form compound 22 (Scheme 6).

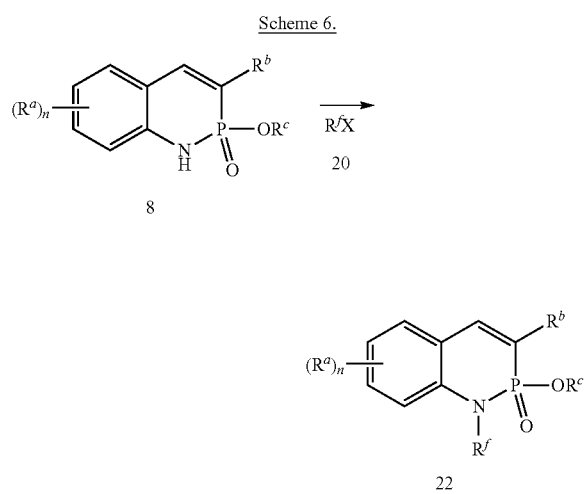

Scheme 6.

With respect to Scheme 6, $R^f$ may be heteroaliphatic, acyl or aliphatic, such as alkyl, alkenyl, alkynyl, cycloalkyl, cycloalkenyl or alkynyl. X may be a suitable leaving group, such as mesylate, tosylate or halide, typically chloride, bromide or iodide. The reaction may be performed in the presence of a base suitable to facilitate the reaction. Suitable bases include, but are not limited to, triethylamine, diisopropylethylamine (DIEA), sodium carbonate, potassium carbonate, 1,8-diazabicyclo[5.4.0]undec-7-ene (DBU) or sodium hydride.

Compounds according to formula XIV may be synthesized from compound 8, according to Scheme 7.

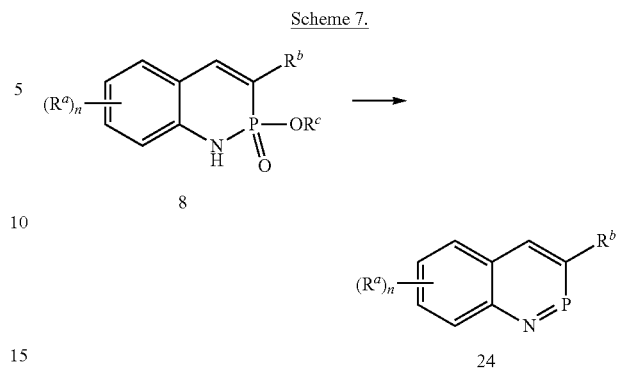

Scheme 7.

With respect to Scheme 7, compound 8 is reacted with a silyl halide, typically, $HSiCl_3$, and a suitable base to form an intermediate (not shown), which is then treated with sodium hydride to form compound 24. The base can be any base which facilitates the reaction, typically triethylamine or DIEA.

Scheme 8 illustrates an exemplary synthesis of certain disclosed compounds according to formula VI:

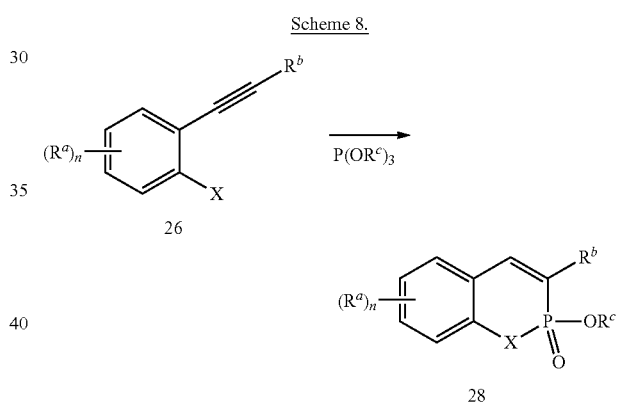

Scheme 8.

With reference to Scheme 8, X may be oxygen or sulfur, and $R^c$ may be aryl, heteroaryl or alkyl. A suitable temperature for the reaction is typically from greater than zero to at least 150 OC, such as from 50° C. to 150° C. or from 75° C. to 125° C., and in certain embodiments 100° C. The reaction is performed in a solvent suitable to facilitate the reaction, such as a non-protic solvent. Suitable solvents include, but are not limited to, pyridine. The reaction may be performed under an inert and/or dry atmosphere, such as under nitrogen or argon.

Certain other embodiments of formula VI may be synthesized according to Scheme 9.

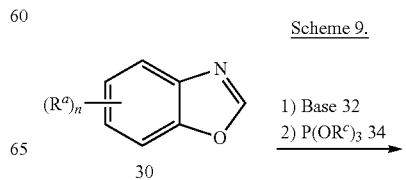

Scheme 9.

-continued

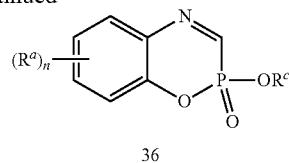

36

With reference to Scheme 9, compound 30 is reacted with a suitable base 32 and then with a phosphite compound 34 to form compound 36. The base 32 may be any base suitable to facilitate the reaction, typically an organometallic base such as butyllithium. The phosphite compound 34 may be a triaryl phosphite, triheteroaryl phosphite or trialkyl phosphite, and is certain embodiments, the phosphite compound 34 is triphenylphosphite.

IV. Method for Using the Compounds

Figure 2:
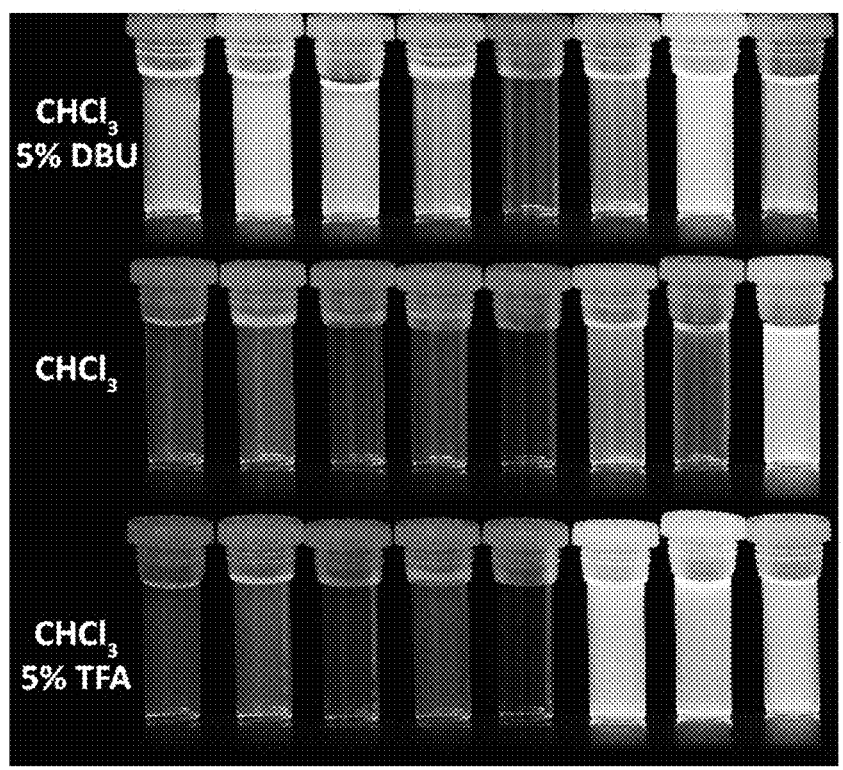
FIG. 2 is a photograph illustrating the fluorescence emissions of exemplary compounds.

Some embodiments of the disclosed compounds are useful as fluorescent probes. The fluorescence of the compounds can be selected by incorporating different substituents on the core structure, and/or by varying the core structure itself. For example, FIG. 1, lines E and I, illustrates the difference in fluorescence between compound II-2 (having formula XIII) and compound I-2 (having formula XII), respectively. A person of ordinary skill in the art will know how to select suitable substituents to change the fluorescence. For example, by replacing an electron withdrawing group with an electron donating group, or vice versa. FIG. 1 illustrates how the fluorescence can vary depending of the combination of core structure and associated substituents. Additionally, the fluorescence may be varied by changing the pH of the solution in which the compound is dissolved. FIGS. 1 and 2 illustrate the change in fluorescence with changing pH.

The disclosed compounds also may be attached to a targeting moiety, such as an antibody, hapten, nucleic acid sequence, polypeptide sequence or small molecule. The disclosed compound may be directly attached to the targeting moiety, or it may be attached through a linker, such as an alkylene oxide linker, typically a PEG linker.

The disclosed compounds may be used in a variety of bioanalytical and/or diagnostic assays. In some embodiments, the disclosed compounds are useful in applications where tunable emission responses are advantageous and/or desired. Such applications include, but are not limited to, labeling cellular mechanisms and/or phenomena for detection by fluorescent microscopy.

The disclosed compounds also may be useful as bioisosteres, for example, in pharmaceutical applications such as drug design. Certain disclosed compounds may be a carbostyril (alpha-quinolone) bioisostere. A bioisostere is a compound or moiety that typically has one or more similar physical and/or chemical properties, such as molecular shape, volume and/or electronic distribution. However, a bioisostere can also enhance or improve certain properties of the molecule, such as improve or prevent unfavorable metabolism, modify solubility, modify lipophilicity, and/or reduce toxicity. The replacement of a carbon by a heteroatom, such as in the presently disclosed compound, may have the effect of reducing or substantially preventing certain enzymes from recognizing the compound. For example, the presently disclosed compounds may have substantially reduced metabolism and/or toxicity compared to a comparable carbostyril compound.

V. Examples

A. General Methods $^1$H and $^{13}$C NMR spectra were obtained on a Varian 300 MHz spectrometer ($^1$H: 299.95 Hz, $^{13}$C: 75.43 Hz), Inova 500 MHz spectrometer ($^1$H: 500.10 MHz, $^{13}$C: 125.75 MHz) or Varian 600 MHz spectrometer ($^1$H: 599.98 MHz, $^{13}$C: 150.87 MHz). Chemical shifts (δ) are expressed in ppm using non-deuterated solvent present in the bulk deuterated solvent (CDCl$_3$: $^1$H 7.26 ppm, $^{13}$C 77.16 ppm; (CD$_3$)$_2$SO: $^1$H 2.5 ppm, $^{13}$C 39.52 ppm). Solvents and reagents were used as purchased from suppliers, unless anhydrous conditions were employed, in which solvents were freshly distilled from sodium/benzophenone under N$_2$ atmosphere (THF) or as purchased in sealed, DriSolv containers (pyridine). Triphenylphosphite was freshly distilled under vacuum before use. Mass spectra were acquired with a Waters LCT Premier ESI-MS in positive mode using acetone as a solvent. UV-Vis spectra were acquired with a Hewlett-Packard 8453 UV-Visible spectrophotometer equipped with a 250 nm cutoff filter. Fluorescence data was acquired with a Horiba Jobin-Yvon FluoroMax-4 fluorescence spectrophotometer. HPLC performed using a JAI Recycling Preparative HPLC (Model LC-9101) with a JAI-GEL-1H preparative column.

B. Synthesis of Compounds According to Formula XII

To a solution of o-ethynyl aniline (0.5 mmol) in dry pyridine (1 mL) was added triphenylphosphite (0.6 mmol) under N$_2$ atmosphere. The mixture was heated reaction to 100° C. for 12 hours. The volatile components were removed and the product was purified by preparative HPLC.

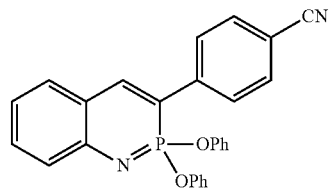 [SMILES: N#Cc1ccc(C2=Cc3ccccc3N=P2(Oc2ccccc2)Oc2ccccc2)cc1]

$^1$H NMR (500 MHz, CDCl$_3$) δ 8.17 (d, J=40.7 Hz, 1H), 7.90 (d, J=8.1 Hz, 2H), 7.76 (d, J=8.0 Hz, 2H), 7.44-7.38 (m, 2H), 7.26 (d, J=8.3 Hz, 1H), 7.21 (t, J=7.8 Hz, 4H), 7.10 (t, J=7.5 Hz, 2H), 6.95 (d, J=7.9 Hz, 5H).
$^{13}$C NMR (126 MHz, CDCl$_3$) δ 151.79, 150.11 (d, J=5.7 Hz), 149.82 (d, J=9.9 Hz), 140.41 (d, J=4.2 Hz), 132.83, 132.10 (d, J=4.7 Hz), 131.45 (d, J=1.7 Hz), 129.74, 127.62 (d, J=6.0 Hz), 125.29, 124.78 (d, J=26.1 Hz), 121.32 (d, J=26.4 Hz), 120.52 (d, J=5.2 Hz), 118.89, 118.67, 111.33, 110.42 (d, J=132.1 Hz).
$^{31}$P NMR (121 MHz, CDCl$_3$) δ 23.79 (d, J=40.8 Hz).

C. Synthesis of Compounds According to Formula XIII

The same procedure was followed for the general cyclization method, but was performed under an ambient atmosphere. Purification proceeded via hot recrystallization from ethyl acetate/hexanes to give crystalline product.

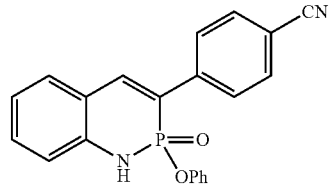 [SMILES: N#Cc1ccc(C2=Cc3ccccc3NP2(=O)Oc2ccccc2)cc1]

Yield: 79%

$^1$H NMR (500 MHz, CDCl$_3$) δ 8.91 (s, 1H), 7.96 (d, J=8.0 Hz, 1H), 7.74 (d, J=8.1 Hz, 1H), 7.66 (d, J=39.1 Hz, 1H), 7.32 (t, J=9.0 Hz, 1H), 7.11-7.04 (m, 1H), 6.99 (dt, J=19.5, 7.5 Hz, 1H), 6.89 (d, J=7.9 Hz, 1H).

$^{13}$C NMR (126 MHz, CDCl$_3$) δ 150.14 (d, J=8.8 Hz), 143.33 (d, J=5.0 Hz), 140.31 (d, J=9.5 Hz), 140.04, 132.65, 131.19 (d, J=59.9 Hz), 129.45, 128.29 (d, J=6.6 Hz), 125.07, 122.75 (d, J=158.6 Hz), 121.40, 121.04 (d, J=4.2 Hz), 119.47 (d, J=14.7 Hz), 118.71, 117.49 (d, J=9.8 Hz), 111.80.

$^{31}$P NMR (202 MHz, CDCl$_3$) δ 10.71 (d, J=38.9 Hz).

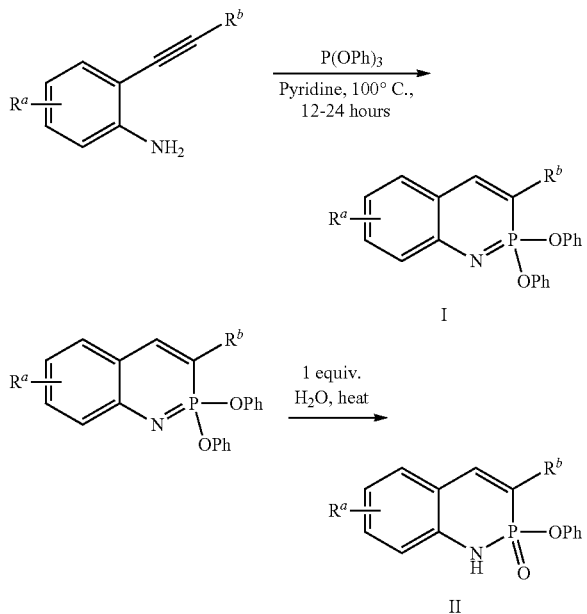

TABLE 1

Synthetic scope of azaphosphinine cyclization.[a]

| Entry | R$^a$ | R$^b$ | Yield (I) | Yield (II) |
|---|---|---|---|---|
| 1 | H | 4-CNPh | 79% | 79% |
| 2 | H | 4-CO$_2$EtPh | 78% | 78% |
| 3 | H | Ph | 60% | 60% |
| 4 | H | 4-MeOPh | 61% | 61% |
| 5 | H | n-Pen | 65% | 65% |
| 6 | H | 2-pyridyl | 70% | 70% |
| 7 | 3,4-OCH$_2$O— | 4-CNPh | 45% | 45% |
| 8 | 4-t-Bu | 2-pyridyl | 55% | 55% |
| 9 | 4-t-Bu | 3,5-(bisCF$_3$)Ph | 40% | 40% |

[a]Conditions: pyridine, 1.1 equiv P(OPh)$_3$, 100° C., 12-24 hours.

Figure 7:
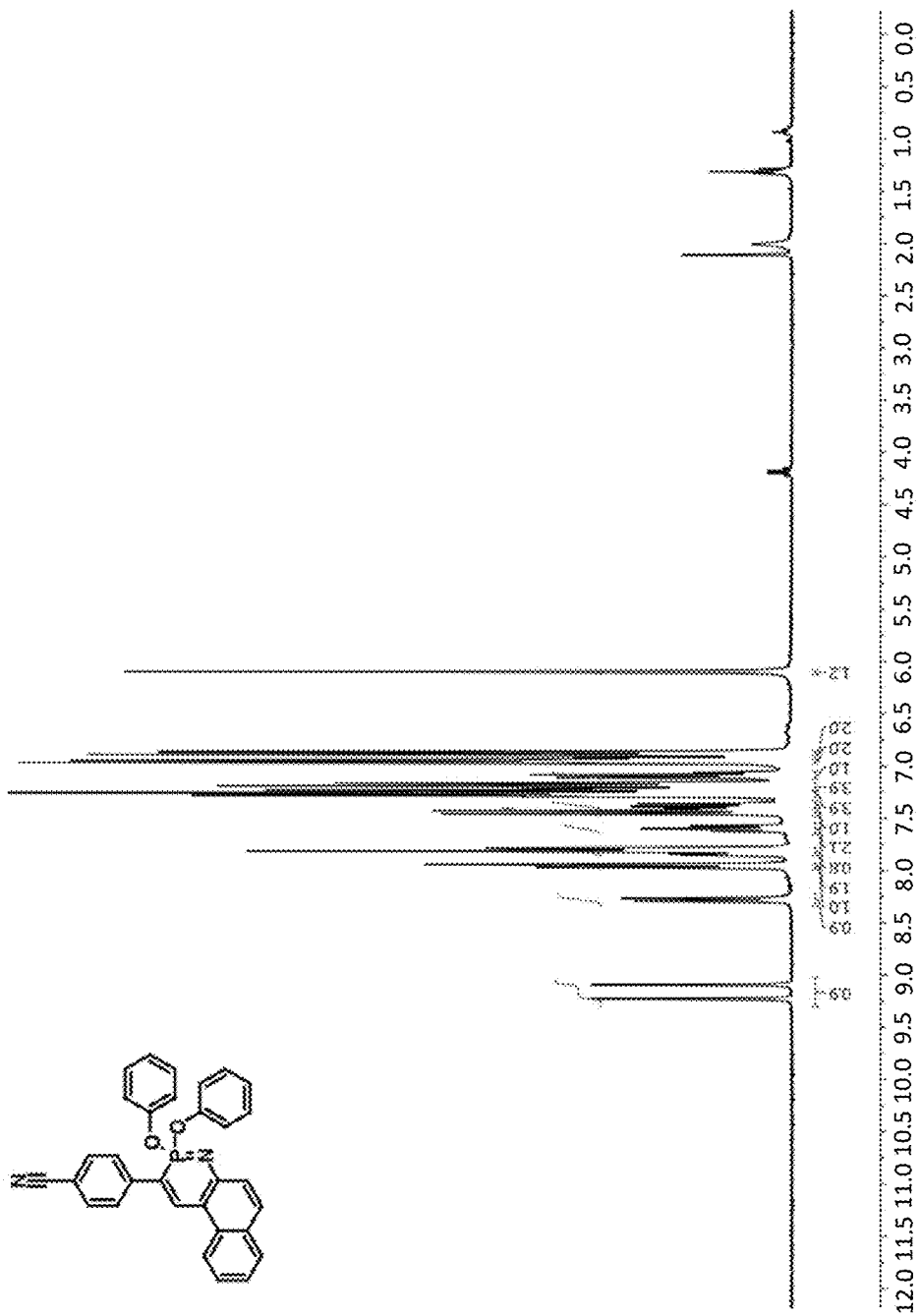
FIG. 7 is an NMR spectra, illustrating the structure of compound I-10.
Figure 8:
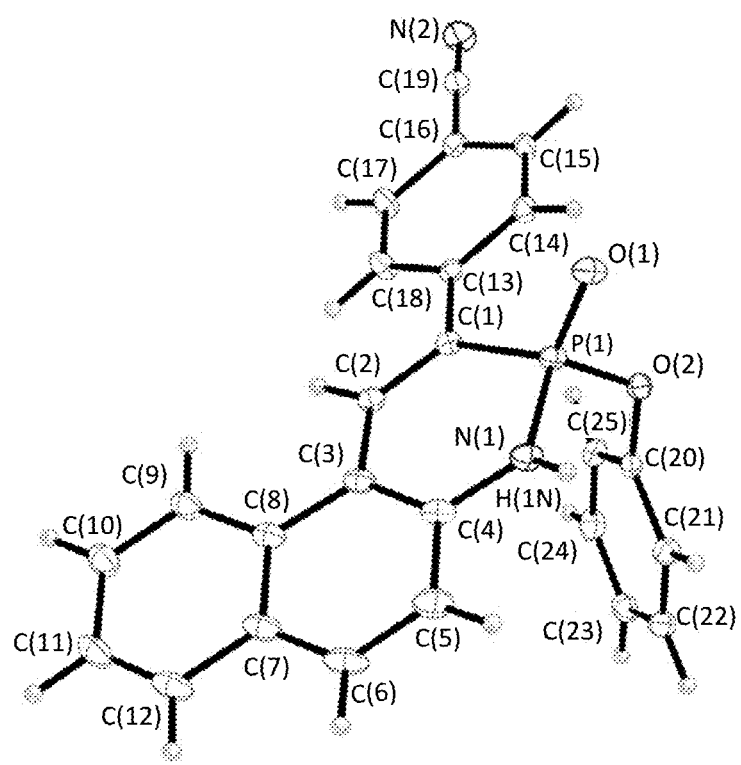
FIG. 8 is a structural representation of compound II-10, based on an X-ray crystal structure, illustrating the position of the naphthyl ring relative to the phosphonimidate bond.

Additionally, entry 10 provides a naphthyl ring in place of the phenyl ring. FIGS. 7 and 8 provide the NMR spectra of compound I-10 and a structural representation of compound II-10 based on the X-ray crystal structure, respectively.

D. Discussion

Phosphonates and their analogs have seen extensive use as ester hydrolysis transition-state mimics, in addition to the ability of phosphonate/phosphonamidate esters to act as ester and amide bioisosteres, not to mention a number of other health-related applications. As a result, new, efficient, metal-free reactions to make phosphorate derivatives of common heterocyclic scaffolds, such as the quinolinone substructure, are a boon for pharmaceutical applications.

The choice of ligands on the phosphorus atom can determine stability of 1,2-λ$^5$-azaphosphinine scaffolds. Carbonaceous residues are generally much more sensitive to oxygen and water than are nitrogenous or oxygenous ligands. Many of the 1,2-λ$^5$-azaphosphinines, especially those with oxygen-based phosphorous ligands, tend to hydrolyze to form the phosphonamidate forms, as compared to the phosphonimidate functionality. This resultant phosphonamidate is much more stable than the -imidate, and gives rise to a number of useful molecules with a variety of pharmaceutical applications.

Disclosed herein is a synthetic approach to assemble the 2-λ$^5$-phosphaquinoline in one step from easily attainable starting materials. By treatment of a 2-ethynyl aniline (for example, accessible from Sonogashira cross-coupling with commercially available 2-iodoanilines) with triphenylphosphite, the disclosed compounds were synthesized in good to modest yields (Table 1). Typically, upon isolation and purification via hot recrystallization in ambient atmosphere, the phosphaquinoline partially hydrolyzed, yielding the phosphaquinolinone form and releasing phenol. However, the phosphonimidate form (A) appeared to be stable at room temperature. This reaction was tolerant to a variety of electron-rich and electron-poor arenes, as well as alkyl functionality attached at the ethynyl.

Figure 3:
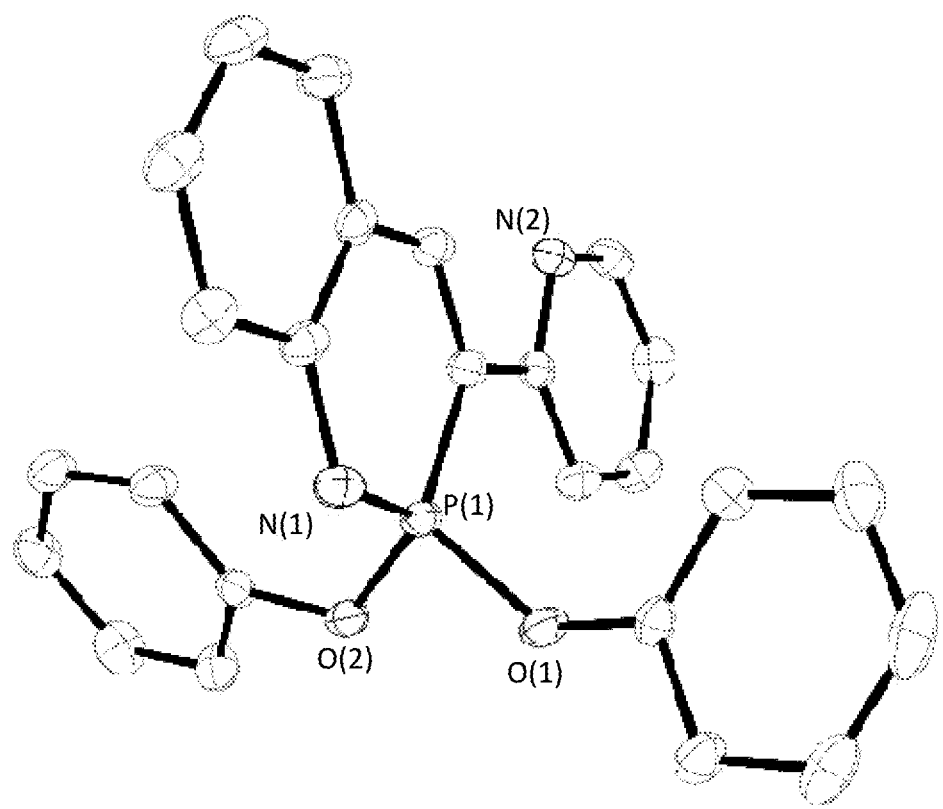
FIG. 3 is a representation of compound 1-6, based on an X-ray crystal structure, illustrating that the angle between the planes of the pyridine and the azaphosphinine ring is 4.7(2)°, measured as torsion angle between pyridine ring and heterocycle.

While there is no disputing aromaticity in λ$^3$-azaphosphinines, extensive studies have examined the delocalization of N=P bonds in phosphorus$^V$ atoms. Single crystal X-ray structures were obtained of I-6 and 11-6, which allowed direct comparison of amino and imino forms (FIGS. 3-6). The imino structure indicated some delocalization, with C=C bond lengths intermediate between benzene and isolated double bonds, and longer than that of carbostyril. The azaphosphinine ring in I-6 also showed small deviations from planarity (FIG. 3, Table 2).

TABLE 2

Selected structural features in phosphaquinolines and phosphaquinolinones.

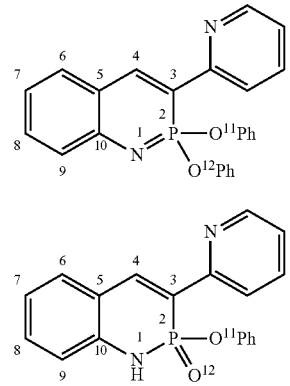

| Entry | I-6 | II-6(1) | II-6(2) |
|---|---|---|---|
| P$^2$—C$^3$ bond length (Å) | 1.760(2) | 1.768(3) | 1.780(3) |
| P$^2$—N$^1$ bond length (Å) | 1.565(2) | 1.638(3) | 1.635(2) |
| C$^3$—C$^4$ bond length (Å) | 1.367(3) | 1.354(4) | 1.341(4) |
| C$^4$—C$^5$ bond length (Å) | 1.446(3) | 1.432(5) | 1.446(4) |
| C$^5$—C$^{10}$ bond length (Å) | 1.425(3) | 1.404(4) | 1.398(5) |
| P$^2$—O$^{11}$ bond length (Å) | 1.5945(17) | 1.605(2) | 1.611(2) |
| P$^2$—O$^{12}$ bond length (Å) | 1.5972(16) | 1.470(2) | 1.4789(19) |
| RMSD (Å) | 0.014 | 0.021 | 0.066 |
| Torsion angle between pyridine and azaphosphinine ring (°) | 4.7(2) | 5.0(3) | 18.8(4) |

Figure 4:
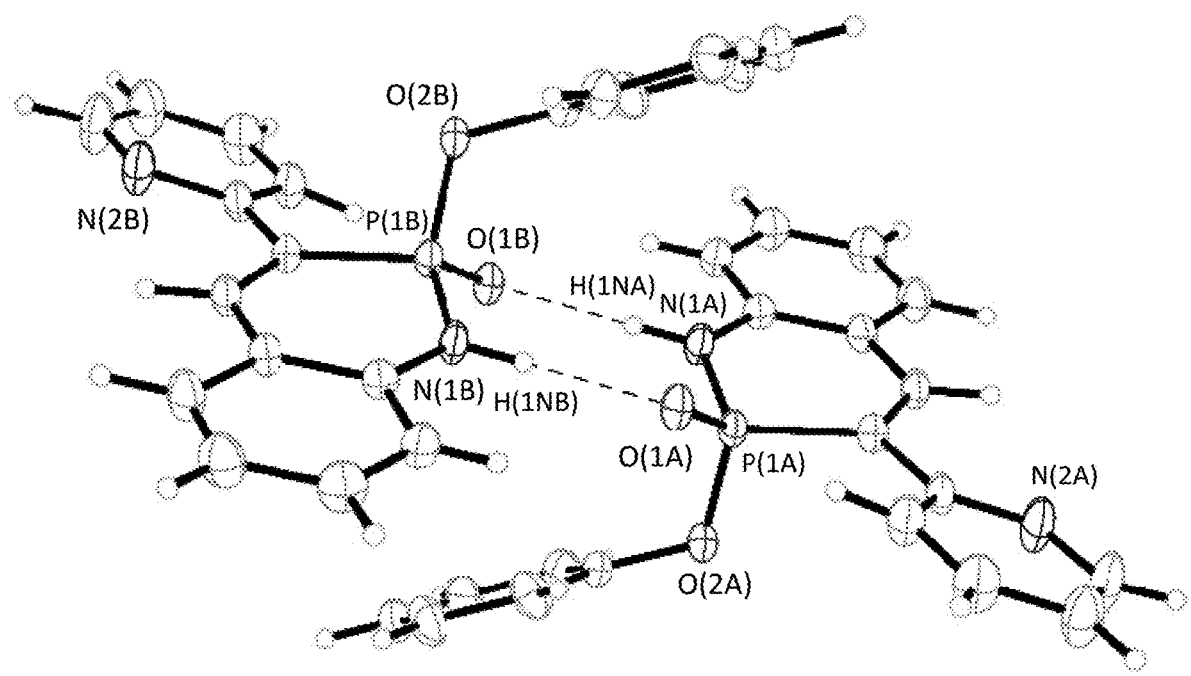
FIG. 4 is an Oak Ridge Thermal Ellipsoid Plot (ORTEP) of the solid state II-6 dimer.

Compound II-6 crystallized in two distinct forms (only one shown in FIG. 4). The two forms exhibited different C=C and P—C bond lengths in the azaphosphinine ring, indicating a range of delocalization of C=C bonds. The two forms also experienced a distinct difference in planarity; the form with a longer C=C bond was more planar within the azaphosphinine ring and more coplanar with the appended pyridyl ring (Table 2).

Except for compounds with a 2-pyridyl substituent, the phosphonimidate compounds tended to hydrolyze when heated in ambient atmosphere to give the phosphonamidate. If the reaction was performed rigorously water-free, and worked up with minimal exposure to ambient atmosphere, the phosphonimidate forms (I) can be isolated for all of the derivatives. Interestingly, the derivative containing an ethyl ester, I-2, did not undergo Staudinger ligation and was quite stable under the 100° C. reaction conditions. This and stability of the phosphonimidate toward hydrolysis at room temperature lent credence to increased stability from delocalization within the heterocycle.

Analysis of crystal structures and computational models indicated that stability of I-6 was likely due to coplanarity of pyridine and the azaphosphinine ring, held by a hydrogen bond between a C—H bond at the 4-position and the pyridine nitrogen (FIG. 3). Without being bound to a particular theory, this conformation was predicted to preclude water addition at phosphorus, as attack would likely occur 180° from the P=N bond. Phosphates typically hydrolyze via an associative mechanism, making a dissociative pathway unlikely. Moreover, with phenyl substituents, an $S_N2$ type displacement (common in alkyl phosphonates) was extremely unlikely.

Structures where the phosphorus atom partially hydrolyzed to form a phosphonamidate-type structure (II) tended to crystallize as dimers between the two enantiomers, forming a complementary association between the N—H and P=O groups (FIG. 4).

Figure 5:
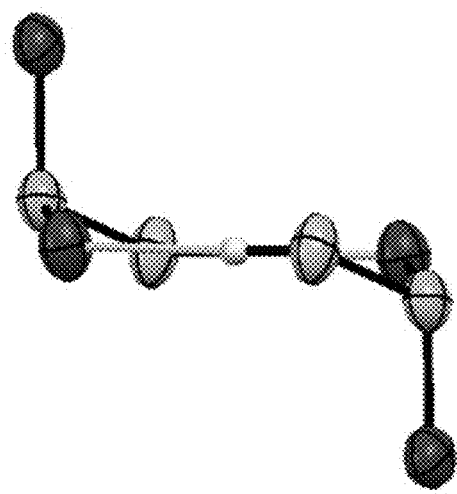
FIG. 5 is an angled view of the plot of FIG. 4, with carbon atoms removed for clarity, illustrating the chair conformation of the hydrogen-bonding ring.
Figure 6:
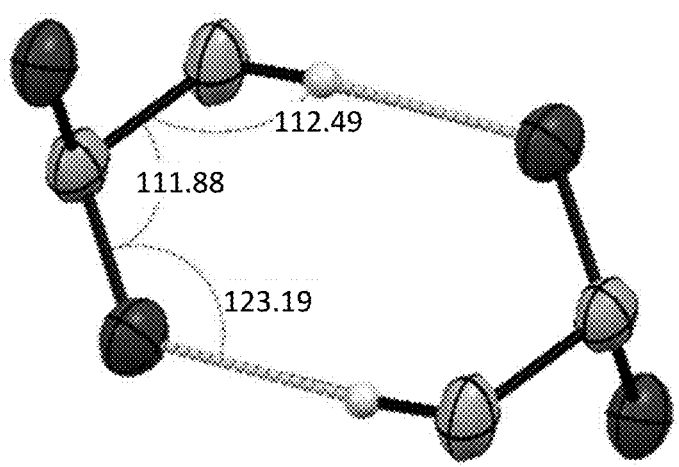
FIG. 6 is the angled view of FIG. 5 viewed from above, with the relevant bond-angles included, illustrating their similarity to idealized chair-conformation angles.

The dimer formed in the solid state is mirrored in solution; compound II-1 possessed a dimerization constant of 133±15 $M^{-1}$ in $CDCl_3$. This corresponded to an energy of 1.5 kcal/mol for each H-bond, which was quite high compared to cis-amides such as pyrrolidone or caprolactam, who experience dimerization constants from 1-5 $M^{-1}$ in $CHCl_3$. Along with the phosphonamidate functionality possessing both a stronger hydrogen bond acceptor (P=O vs C=O) and hydrogen bond donor (Phosphonamidate N—H $pK_a$≈5, amide $pK_a$≈14) than amides, the non-coplanar arrangement of donor and acceptor and lower directional preference of P=O donors allowed the pseudo 6-membered ring to adopt a chair-like configuration and minimize repulsive secondary interactions (FIG. 5). As a result, this dimer deviated from the trends previously reported, where each attractive interaction gave −1.88 kcal/mol of energy to ΔG, and each repulsive secondary interaction gave +0.74 kcal/mol. Following the same schema, the two repulsive secondary interactions in the present dimer yielded only +0.76 kcal/mol of destabilization, about half of what was expected.

The compounds gave fluorescence emissions similar to those of carbostyril. (3-Ph-carbostyril ex: 345 nm, em: 410 nm; II-3 ex: 354 nm, em: 427 nm). Significant differences included a more dramatic solvatochromic effect on fluorescence, dependent on substitution (II-1 $CHCl_3$ em: 430 nm, MeCN em: 450 nm, II-4 MeCN & $CHCl_3$ em: 411 nm), and an easily deprotonated N—H yielding a red-shifted fluorescent response (TEA+II-1 in $CHCl_3$ ex: 360 nm, em: 542 nm; Neutral form: ex: 345 nm, em: 430 nm) with a surprisingly large Stokes shift of 180 nm.

The only scaffold which responded to the addition of acid was one containing a 2-pyridyl substituent, which directly corresponded to protonation of the pyridine. The N—H proton of the NH—P(OPh)=O functionality is fairly acidic, and easily removed via treatment with organic bases such as DBU. The fluorescent emission red-shifted for all of the scaffolds upon treatment with base, and in the case of II-1, resulted in a Stokes shift of 180 nm. The fluorophore II-7 gave substitution patterns that were followed for both red-shift and quantum yield optimization of carbostyril fluorophores. Following the guidelines within the scaffold, with placement of electron donating groups in the 6- and 7-positions, and an electron-withdrawing group in the 3-position, yielded a fluorophore with an emission of 505 nm and a quantum yield of 45% in $CHCl_3$.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A compound of formula I

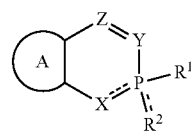

or a pharmaceutically acceptable salt thereof, wherein:
ring A is aryl;
X is $NR^3$;
Y is $CR^4$;
Z is $CR^4$;
$R^1$ is —OH, aryl, heteroaryl, —O-aliphatic, —O-aryl, —O-heteroaryl, —O-heterocyclic, or —O-heteroaliphatic;
$R^2$ is oxo (=O), or =S;
$R^3$ is H, aliphatic, heteroaliphatic, heterocyclic, heteroaryl, acyl, carboxyl ester, or a lone pair of electrons;
each $R^4$ independently is H, aliphatic, heteroaliphatic, aryl, heterocyclic, heteroaryl, halo, CN, $NO_2$, sulfonyl, amino, carboxyl, carboxyl ester, aminosulfonyl, or aminocarbonyl; and
"---" represents a bond that may or may not be present.

2. The compound of claim 1, wherein $R^1$ is —OH, aryl, heteroaryl, —O-alkyl, —O-alkenyl, —O-alkynyl, —O-cycloalkyl, —O-cycloalkenyl, —O-cycloalkynyl, —O-aryl, —O-heteroaryl, —O-heterocyclic, —O-heterocycloaliphatic, —O-heteroalkyl or —O— heterocycloalkyl.

3. The compound of claim 1, wherein $R^2$ is oxo.

4. The compound of claim 1, wherein $R^3$ is H, alkyl, alkenyl, alkynyl, cycloalkyl, cycloalkenyl, cycloalkynyl, heteroaryl, heterocyclic, heterocycloaliphatic, heteroalkyl, heterocycloalkyl, carboxyl ester, or a lone pair of electrons.

5. The compound of claim 1, wherein each $R^4$ independently is H, alkyl, alkenyl, alkynyl, haloalkyl, cycloalkyl, cycloalkenyl, cycloalkynyl, aryl, heteroaryl, heterocyclic, heterocycloaliphatic, heteroalkyl, heterocycloalkyl, halo, CN, $NO_2$, sulfonyl, amino, carboxyl, aminosulfonyl, aminocarbonyl, or —$CO_2R$ where R is aryl or heteroaryl.

6. The compound of claim 1, wherein ring A is phenyl, or naphthyl.

7. The compound of claim 6, wherein ring A is phenyl.

8. The compound of claim 1, wherein Z is CH.

9. The compound of claim 1, wherein each $R^4$ independently is alkyl, cycloalkyl, aryl or heteroaryl.

10. The compound of claim 9, wherein each $R^4$ independently is 2-pyridyl, phenyl, 4-NC-phenyl, 4-EtOC(O)-phenyl, 4-methoxyphenyl, 3,5-bis(trifluoromethyl)phenyl, methyl, ethyl, n-propyl, isopropyl, cyclopropyl, n-butyl, isobutyl, sec-butyl, tert-butyl, cyclobutyl, n-pentyl or cyclopentyl.

11. The compound of claim 1, wherein $R^1$ is —O-phenyl, methoxy, ethoxy, propoxy, cyclopropoxy, isopropoxy, butoxy, isobutoxy, tert-butoxy, phenyl, pyridyl, thienyl.

12. The compound of claim 11, wherein $R^1$ is —O-phenyl, phenyl, or thienyl.

13. The compound of claim 11, wherein $R^1$ is —O-phenyl, and $R^2$ is oxo.

14. The compound of claim 1, wherein the compound has a structure according to

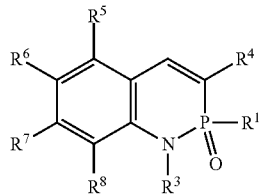

wherein
$R^5$, $R^6$, $R^7$ and $R^8$ independently are H, aliphatic, haloalkyl, heteroaliphatic, aryl, heterocyclic, heteroaryl, —O-aliphatic, —O-heteroaliphatic, —O-heterocyclic, —O-heteroaryl, —O-aryl, halo, OH, CN, $NO_2$, sulfonyl, amino, carboxyl, carboxyl ester, aminosulfonyl, or aminocarbonyl or any two adjacent groups together form an aliphatic, heterocyclic, aryl or heteroaryl ring.

15. The compound of claim 1, wherein the compound has a structure according to

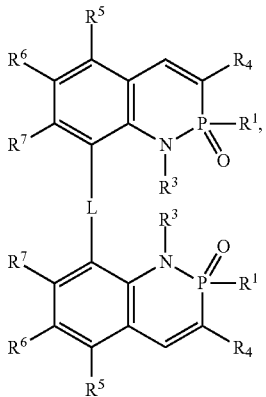

wherein L is a bond, aliphatic, aryl, heteroaryl, heteroaliphatic, or heterocyclic; and each $R^5$, $R^6$, and $R^7$ independently is H, alkyl, alkenyl, alkynyl, cycloalkyl, cycloalkenyl, cycloalkynyl, haloalkyl, aryl, heteroaryl, heterocyclic, heterocycloaliphatic, heteroalkyl, heterocycloalkyl, —O-alkyl, —O-alkenyl, —O-alkynyl, —O-heteroaliphatic, —O-heterocyclic, —O— heteroaryl, —O-aryl, halo, CN, $NO_2$, sulfonyl, amino, carboxyl, carboxyl ester, aminosulfonyl, or aminocarbonyl or any two adjacent groups together form an aliphatic, heterocyclic, aryl or heteroaryl ring.

16. The compound of claim 15, wherein:
L is phenyl; or
each $R^5$, $R^6$, and $R^7$ is H; or
L is phenyl and each $R^5$, $R^6$, and $R^7$ is H.

17. The compound of claim 1, wherein the compound is selected from:
 4-(2-oxido-2-phenoxy-1H-benzo[e][1,2]azaphosphinin-3-yl)benzonitrile;
 ethyl 4-(2-oxido-2-phenoxy-1H-benzo[e][1,2]azaphosphinin-3-yl)benzoate;
 2-phenoxy-3-phenyl-1H-benzo[e][1,2]azaphosphinine 2-oxide;
 3-(4-methoxyphenyl)-2-phenoxy-1H-benzo[e][1,2]azaphosphinine 2-oxide;
 3-pentyl-2-phenoxy-1H-benzo[e][1,2]azaphosphinine 2-oxide;
 2-phenoxy-3-(pyridin-2-yl)-1H-benzo[e][1,2]azaphosphinine 2-oxide;
 4-(2-oxido-2-phenoxy-1H-[1,3]dioxolo[4',5':4,5]benzo[1,2-e][1,2]azaphosphinin-3-yl)benzonitrile;
 6-(tert-butyl)-2-phenoxy-3-(pyridin-2-yl)-1H-benzo[e][1,2]azaphosphinine 2-oxide;
 3-(3,5-bis(trifluoromethyl)phenyl)-6-(tert-butyl)-2-phenoxy-1H-benzo[e][1,2]azaphosphinine 2-oxide;
 4-(3-oxido-3-phenoxy-4H-naphtho[1,2-e][1,2]azaphosphinin-2-yl)benzonitrile;
 4-(2-oxido-2-phenoxy-1H-naphtho[2,3-e][1,2]azaphosphinin-3-yl)benzonitrile;
 4-(2-oxido-2-phenoxy-1H-naphtho[2,1-e][1,2]azaphosphinin-3-yl)benzonitrile;
 4,4'-(1,4-phenylenebis(2-oxido-2-phenoxy-1H-benzo[e][1,2]azaphosphinine-8,3-diyl))dibenzonitrile;
 4,4'-(1,3-phenylenebis(2-oxido-2-phenoxy-1H-benzo[e][1,2]azaphosphinine-8,3-diyl))dibenzonitrile;
 4,4'-(1,2-phenylenebis(2-oxido-2-phenoxy-1H-benzo[e][1,2]azaphosphinine-8,3-diyl))dibenzonitrile;
 4-(1-benzyl-2-oxido-2-phenoxy-1H-benzo[e][1,2]azaphosphinin-3-yl)benzonitrile;
 4-(1-acetyl-2-oxido-2-phenoxy-1H-benzo[e][1,2]azaphosphinin-3-yl)benzonitrile;
 4-(2-oxido-2-phenyl-1H-benzo[e][1,2]azaphosphinin-3-yl)benzonitrile;
 4-(2-oxido-2-(thiophen-3-yl)-1H-benzo[e][1,2]azaphosphinin-3-yl)benzonitrile;
 4-(1-methyl-2-oxido-2-phenoxy-1H-benzo[e][1,2]azaphosphinin-3-yl)benzonitrile;
 4-(1-ethyl-2-oxido-2-phenoxy-1H-benzo[e][1,2]azaphosphinin-3-yl)benzonitrile;
 4-(1-isopropyl-2-oxido-2-phenoxy-1H-benzo[e][1,2]azaphosphinin-3-yl)benzonitrile; or
 4-(2-oxido-2-(thiophen-2-yl)-1H-benzo[e][1,2]azaphosphinin-3-yl)benzonitrile.

* * * * *